(12) United States Patent
Bishop

(10) Patent No.: US 7,942,906 B2
(45) Date of Patent: May 17, 2011

(54) SPINAL STABILIZATION SYSTEM FOR THE STABILIZATION AND FIXATION OF THE LUMBAR SPINE AND METHOD FOR USING SAME

(75) Inventor: Randolph C. Bishop, Savannah, GA (US)

(73) Assignee: Neurospine Innovations And Solutions, LLC, Savannah, GA (US)

( * ) Notice: Subject to any disclaimer, the term of this patent is extended or adjusted under 35 U.S.C. 154(b) by 600 days.

(21) Appl. No.: 12/029,268

(22) Filed: Feb. 11, 2008

(65) Prior Publication Data

US 2008/0195150 A1 Aug. 14, 2008

Related U.S. Application Data

(60) Provisional application No. 60/900,524, filed on Feb. 12, 2007.

(51) Int. Cl.
*A61B 17/70* (2006.01)

(52) U.S. Cl. ......... 606/257; 606/246; 606/267; 606/277

(58) Field of Classification Search .................. 606/246, 606/250–279, 300–321
See application file for complete search history.

(56) References Cited

U.S. PATENT DOCUMENTS

| | | | |
|---|---|---|---|
| 4,611,581 A | 9/1986 | Steffee | |
| 4,805,602 A | 2/1989 | Puno et al. | |
| 5,129,900 A | 7/1992 | Asher et al. | |
| 5,474,555 A | 12/1995 | Puno et al. | |
| 5,569,247 A | 10/1996 | Morrison | |
| 5,575,792 A | 11/1996 | Errico et al. | |
| 5,643,263 A | 7/1997 | Simonson | |
| 5,683,392 A | 11/1997 | Richelsoph et al. | |
| 5,688,274 A | 11/1997 | Errico et al. | |
| 5,690,630 A | 11/1997 | Errico et al. | |
| 5,725,527 A | 3/1998 | Biedermann et al. | |
| 5,741,255 A | 4/1998 | Krag et al. | |
| 5,797,911 A | 8/1998 | Sherman et al. | |
| 5,863,293 A | 1/1999 | Richelsoph | |
| 5,879,350 A | 3/1999 | Sherman et al. | |
| 5,885,285 A | 3/1999 | Simonson | |
| 5,891,145 A | 4/1999 | Morrison et al. | |
| 5,964,760 A | 10/1999 | Richelsoph | |
| 6,010,503 A | 1/2000 | Richelsoph et al. | |
| 6,019,759 A | 2/2000 | Regozinski | |
| 6,022,350 A | 2/2000 | Ganem | |
| 6,074,391 A | 6/2000 | Metz-Stavenhagen et al. | |
| 6,077,262 A | 6/2000 | Schlapfer et al. | |
| 6,090,111 A | 7/2000 | Nichols | |
| 6,132,430 A | 10/2000 | Wagner | |
| 6,248,105 B1 | 6/2001 | Schlapfer et al. | |
| 6,290,703 B1 | 9/2001 | Ganem | |

(Continued)

*Primary Examiner* — Eduardo C Robert
*Assistant Examiner* — Christina Negrelli
(74) *Attorney, Agent, or Firm* — Ballard Spahr LLP

(57) ABSTRACT

The present invention includes a system and method for the stabilization and fixation of the lumbar spine. Another aspect of the invention includes a system and method for the stabilization and fixation of the lumbar spine in a minimally invasive manner. The system can include a plurality of pedicle screws, a support rod, a plurality of rod clamps, and a plurality of coupling members. In one aspect, each coupling member can be configured to engage a proximal portion of a pedicle screw and can have a socket portion that is configured to receive a socket engaging portion of the rod clamp, such that the coupling member and the pedicle screw can be pivoted three-dimensionally relative to the rod clamp and the support rod.

27 Claims, 23 Drawing Sheets

U.S. PATENT DOCUMENTS

| | | |
|---|---|---|
| 6,451,021 B1 | 9/2002 | Ralph et al. |
| 6,471,705 B1 | 10/2002 | Biedermann et al. |
| 6,524,315 B1 | 2/2003 | Selvitelli et al. |
| 6,540,749 B2 | 4/2003 | Schafer et al. |
| 6,547,790 B2 | 4/2003 | Harkey, III et al. |
| 6,565,565 B1 | 5/2003 | Yuan et al. |
| 6,596,008 B1 | 7/2003 | Kambin |
| 6,626,906 B1 * | 9/2003 | Young .......................... 606/278 |
| 2002/0120272 A1 | 8/2002 | Yuan et al. |

* cited by examiner

SPINAL STABILIZATION SYSTEM FOR THE STABILIZATION AND FIXATION OF THE LUMBAR SPINE AND METHOD FOR USING SAME

CROSS-REFERENCE TO RELATED APPLICATION

This application claims the benefit of U.S. Provisional Patent Application No. 60/900,524 (filed Feb. 12, 2007). The entire content of the foregoing application is hereby expressly incorporated by reference herein.

FIELD OF THE INVENTION

This application relates to surgical systems, assemblies, devices, and methods that may be used for less invasive and/or minimally invasive surgery, and in particular relates to surgical systems, assemblies, devices, and methods that may relate to gaining access to and/or treatment of the spine.

BACKGROUND

Back pain, particularly in the "small of the back" or lumbosacral region is a common ailment. In many cases, the pain severely limits a person's functional ability and quality of life. Such pain can result from a variety of spinal pathologies. Through disease or injury, the laminae, spinous process, articular processes, or facets of one or more vertebral bodies can become damaged, such that the vertebrae no longer articulate or properly align with each other. This can result in an undesired anatomy, loss of mobility, and pain or discomfort.

One type of conventional treatment of spinal pathologies is spinal stabilization, also known as intervertebral stabilization. Intervertebral stabilization desirably prevents relative motion between vertebrae of the spine. By preventing movement, pain can be reduced. Stabilization can be accomplished by various methods. One method of stabilization is spinal fusion. Another method of stabilization is fixation of any number of vertebrae to stabilize and prevent movement of the vertebrae. In addition, where compression or subsidence of the disc and/or facet joints has occurred, the physician can utilize fusion devices such as pedicle screw and rods systems, or interbody fusion cages, to elevate or "jack up" the compressed level, desirably obtaining a more normal anatomical spacing between the vertebral bodies.

Various devices are known for fixing the spine and/or sacral bone adjacent the vertebra, as well as attaching devices used for fixation, are known in the art including: U.S. Pat. No. 6,290,703, to Ganem, for Device for Fixing the Sacral Bone to Adjacent Vertebrae During Osteosynthesis of the Backbone; U.S. Pat. No. 6,596,008, to Kambin, III, et al., for Method and Instruments for Percutaneous Arthroscopic Disc Removal, Bone Biopsy and Fixation of the Vertebral; U.S. Pat. No. 6,547,790, to Harkey, III, et al., for Orthopaedic Rod/Plate Locking Mechanisms and Surgical Methods; U.S. Pat. No. 6,074,391, to Metz-Stavenhagen, et al., for Receiving Part for a Retaining Component of a Vertebral Column Implant; U.S. Pat. No. 5,569,247, to Morrison, for Enhanced Variable Angle Bone Bolt; U.S. Pat. No. 5,891,145, to Morrison, et al., for Multi-Axial Screw; U.S. Pat. No. 6,090,111, to Nichols, for Device for Securing Spinal Rods; U.S. Pat. No. 6,451,021, to Ralph, et al., for Polyaxial Pedicle Screw Having a Rotating Locking Element; U.S. Pat. No. 5,683,392, to Richelsoph, et al., for Multi-Planar Locking Mechanism for Bone Fixation; U.S. Pat. No. 5,863,293, to Richelsoph, for Spinal Implant Fixation Assembly; U.S. Pat. No. 5,964,760, to Richelsoph, for Spinal Implant Fixation Assembly; U.S. Pat. No. 6,010,503, to Richelsoph, et al., for Locking Mechanism; U.S. Pat. No. 6,019,759, to Rogozinski, for Multi-Directional Fasteners or Attachment Devices for Spinal Implant Elements; U.S. Pat. No. 6,540,749, to Schafer, et al., for Bone Screw; U.S. Pat. No. 6,077,262, to Schlapfer, for Posterior Spinal Implant; U.S. Pat. No. 6,248,105, to Schlapfer, et al., for Device for Connecting a Longitudinal Support with a Pedicle Screw; U.S. Pat. No. 6,524,315, to Selvitelli, et al., for Orthopaedic Rod/Plate Locking Mechanism; U.S. Pat. No. 5,797,911, to Sherman, et al., for Multi-Axial Bone Screw Assembly; U.S. Pat. No. 5,879,350, to Sherman, et al., for Multi-Axial Bone Screw Assembly; U.S. Pat. No. 5,885,285, to Simonson, For Spinal Implant Connection Assembly; U.S. Pat. No. 5,643,263, to Simonson for Spinal Implant Connection Assembly; U.S. Pat. No. 6,565,565, to Yuan, et al., for Device for Securing Spinal Rods; U.S. Pat. No. 5,725,527, to Biederman, et al., for Anchoring Member; U.S. Pat. No. 6,471,705, to Biederman, et al., for Bone Screw; U.S. Pat. No. 5,575,792, to Errico, et al., for Extending Hook and Polyaxial Coupling Element Device for Use with Top Loading Rod Fixation Devices; U.S. Pat. No. 5,688,274, to Errico, et al., for Spinal Implant Device having a Single Central Rod and Claw Hooks; U.S. Pat. No. 5,690,630, to Errico, et al., for Polyaxial Pedicle Screw; U.S. Pat. No. 6,022,350, to Ganem, for Bone Fixing Device, in Particular for Fixing to the Sacrum during Osteosynthesis of the Backbone; U.S. Pat. No. 4,805,602, to Puno, et al., for Transpedicular Screw and Rod System; U.S. Pat. No. 5,474,555, to Puno, et al., for Spinal Implant System; U.S. Pat. No. 4,611,581, to Steffee, for Apparatus for Straightening Spinal Columns; U.S. Pat. No. 5,129,900, to Asher, et al., for Spinal Column Retaining Method and Apparatus; U.S. Pat. No. 5,741,255, to Krag, et al., for Spinal Column Retaining Apparatus; U.S. Pat. No. 6,132,430, to Wagner, for Spinal Fixation System; U.S. Publication No. 2002/0120272, and to Yuan, et al., for Device for Securing Spinal Rods.

Further, spinal surgery presents significant difficulties to the physician who is attempting to reduce chronic back pain or correct spinal deformities without introducing additional trauma due to the surgical procedure itself. In order to access the vertebrae to perform spinal procedures, the physician is typically required to make large incisions and cut or strip muscle tissue surrounding the spine. In addition, care must be taken not to injure nerve tissue in the area. Consequently, traditional surgical procedures of this type carry high risks of scarring, pain, significant blood loss, and extended recovery times.

Systems, assemblies, devices, and methods for performing less invasive and/or minimally invasive techniques have been proposed to reduce the trauma of posterior spinal surgery by reducing the size of the incision and the degree of muscle stripping in order to access the vertebrae. A number of different such systems, assemblies, devices, and methods are known, each having certain advantages and disadvantages. However, there is an ongoing need to provide alternative systems, assemblies, devices, and methods for gaining access to and/or treating the spine of a patient.

SUMMARY

The present invention includes a spinal stabilization system and method for the stabilization and fixation of the lumbar spine. Another aspect of the invention includes a spinal stabilization system and method for the stabilization and fixation of the lumbar spine in a minimally invasive manner.

According to one embodiment of the invention, the spinal stabilization system comprises a plurality of pedicle screws, a support rod, a plurality of rod clamps, and a plurality of coupling members. In one exemplary aspect, each pedicle screw can have a distal threaded portion that is configured to engage bone of a subject's spinal column. In another aspect, each rod clamp can comprise a rod mounting portion and a socket engaging portion. In this aspect, the coupling member is configured to engage a proximal portion of the pedicle screw. In a further aspect, the coupling member can have a socket portion that is configured to receive a socket engaging portion of the rod clamp. When received in this fashion, the coupling member and the pedicle screw can be pivoted three-dimensionally relative to the rod clamp and the support rod.

In one exemplary aspect, the plurality of pedicle screws can comprise a first and second pedicle screw and the plurality of rod clamps can comprise a first rod clamp and a second rod clamp. Further, in this exemplary aspect, each coupling member can comprise a first coupling member and a second coupling member. In this aspect, the first coupling member can engage a proximal portion of the first pedicle screw and can be configured to receive the socket engaging portion of the first rod clamp so that the first coupling member and first pedicle screw can be pivoted three-dimensionally relative to the first rod clamp and the support rod. Similarly, the second coupling member can engage a proximal portion of the second pedicle screw and can be configured to receive the socket engaging portion of the second rod clamp such that the second coupling member and second pedicle screw can be pivoted three-dimensionally relative to the second rod clamp and the support rod.

Other apparatus, methods, and aspects and advantages of the invention will be discussed with reference to the Figures and to the detailed description of the preferred embodiments.

BRIEF DESCRIPTION OF THE FIGURES

The accompanying drawings, which are incorporated in and constitute a part of this specification, illustrate several aspects described below and together with the description, serve to explain the principles of the invention. Like numbers represent the same elements throughout the figures.

DETAILED DESCRIPTION OF THE INVENTION

The present invention can be understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an," and "the" include plural referents unless the context clearly dictates otherwise. Thus, for example, reference to "a pedicle screw" can include two or more such pedicle screws unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Figure 1:
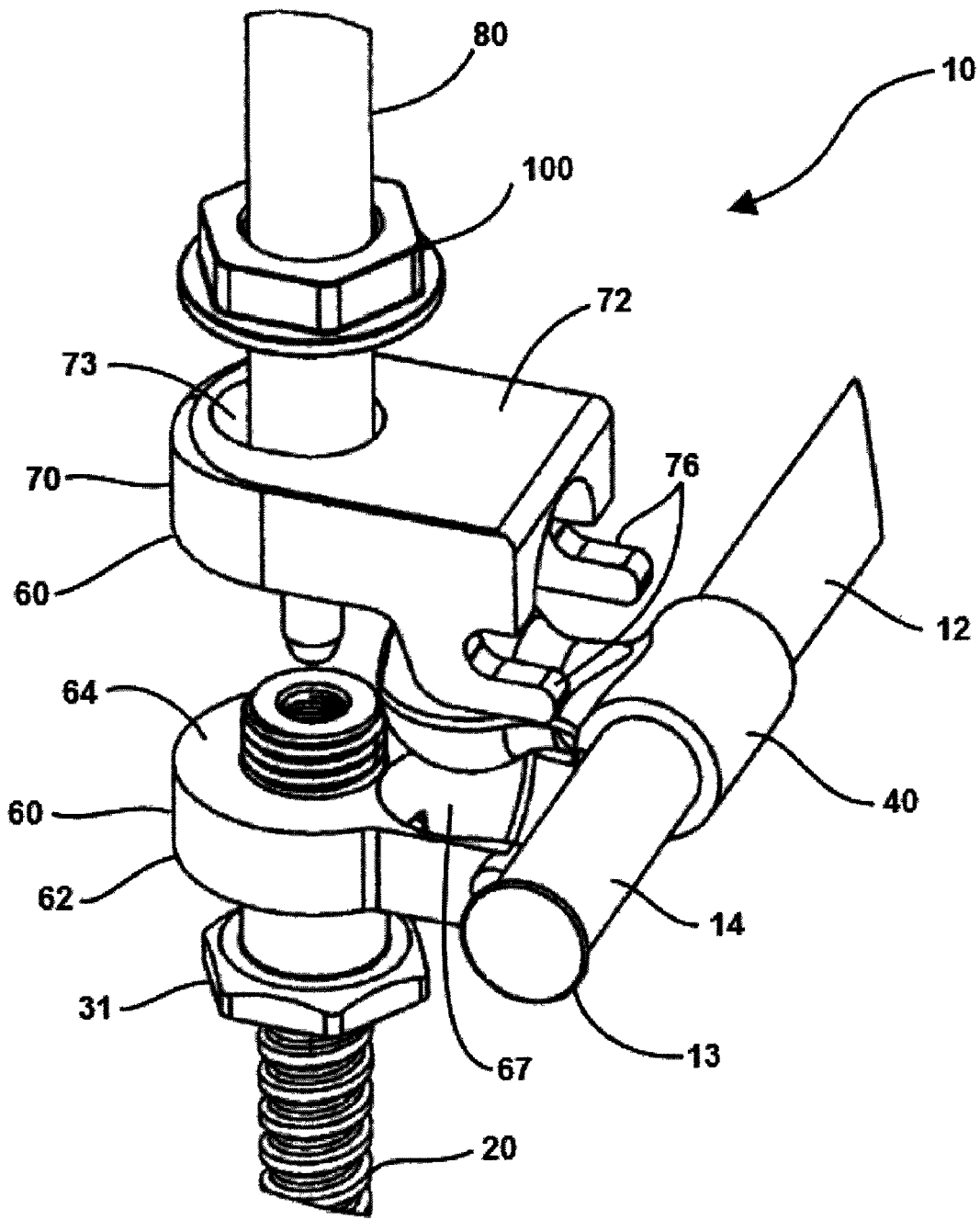
FIG. 1 is a partial exploded perspective view of one embodiment of the spinal stabilization system of the present invention, showing a support rod; a coupling member, a pedicle screw, a rod clamp, a fastener, and an extension rod.
Figure 2:
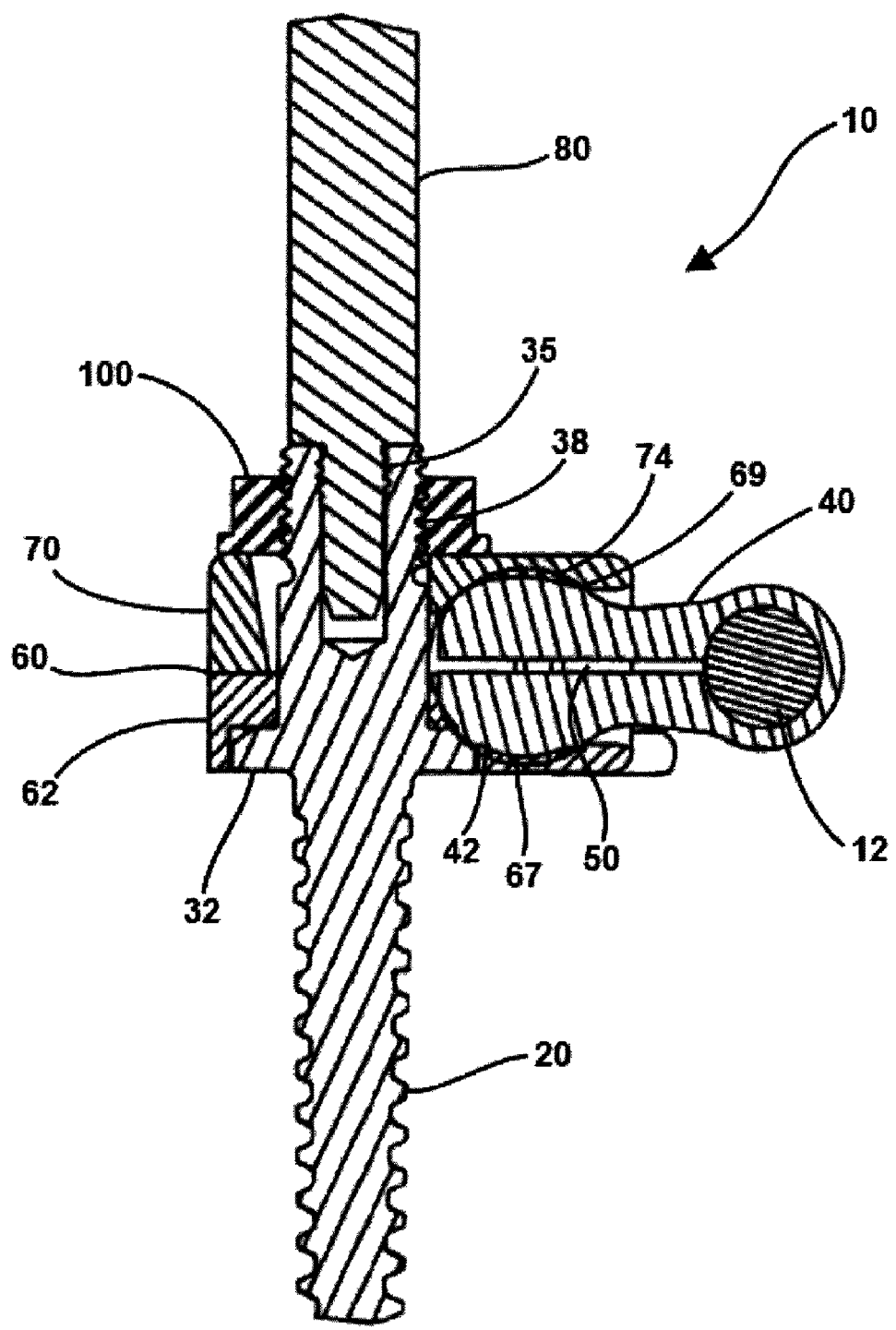
FIG. 2 is a partial cross-sectional view of the spinal stabilization system shown in a second clamped configuration prior to the removal of the extension rod.

FIGS. 1 and 2 illustrate an exemplary embodiment of the spinal stabilization system 10 of the present invention. Although the exemplary spinal stabilization system 10 described below is designed primarily for use in spinal applications, one skilled in the art will appreciate that the structure, features, and principles of the exemplary stabilization system may be employed in other bone fixation modalities. Non-limiting examples of optional applications of the spine stabilization system 10 described herein include, without limitation, long bond fracture fixation/stabilization, small bone stabilization, lumbar spine as well as thoracic stabilization/fusion, cervical spine compression/fixation, and the like.

The illustrated exemplary spinal stabilization system 10 can comprise a plurality of pedicle screws 20 configured for engaging bone; an elongated support rod 12; a plurality of rod clamps 40 for selective positioning thereon the support rod; a plurality of coupling members 60 configured to couple the rod clamps to a portion of the pedicle screws; and a plurality of extension rods 80 that are releasably coupled to a portion of the pedicle screws. In one example and not meant to be limiting, the plurality of pedicle screws 20 can comprise a first pedicle screw 20' and a second pedicle screw 20"; the plurality of rod clamps 40 can comprise a first rod clamp 40' and a second rod clamp 40"; the plurality of coupling members 60 can comprise a first coupling member 60' and a second coupling member 60"; and the plurality of extension rods 80 can comprise a first extension rod 80' and a second extension rod 80". As one skilled in the art will appreciate, this is not meant as a limitation, as any desired number of the respective pedicle screws 20, rod clamps 40, coupling members 60, extension rods and/or support rods can be used as desired.

In one exemplary aspect, the elongated support rod 12 is substantially rigid. In one exemplary aspect, the support rod may be cylindrically shaped. In another aspect, a distal end of the elongated support rod 12 can define a raised lip 13 that has a diameter that is greater than the diameter of the elongate body 14 of the support rod.

Figure 3A:
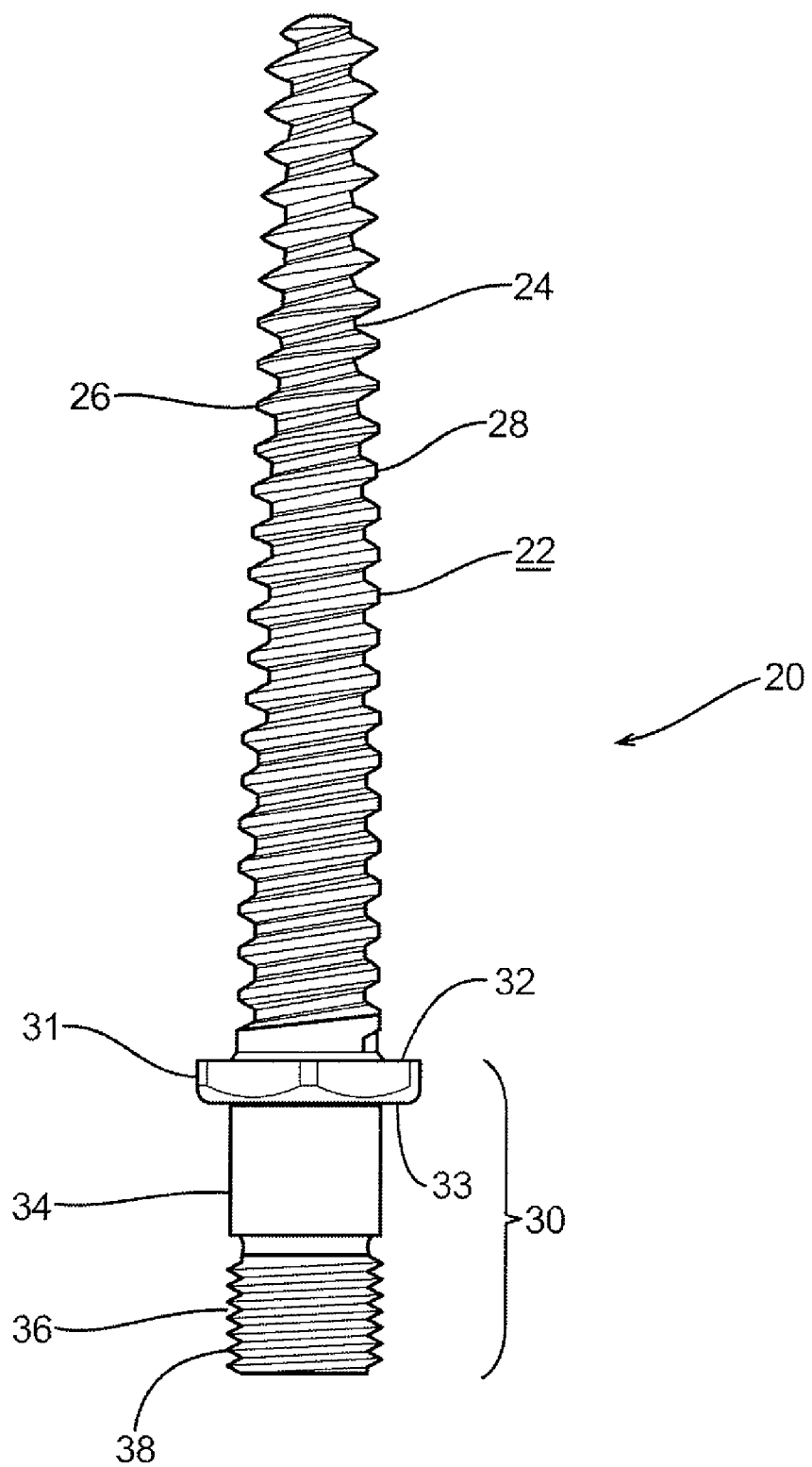
FIG. 3A is a side elevational view of an exemplary embodiment of a pedicle screw for the spinal stabilization system of the present invention.
Figure 3B:
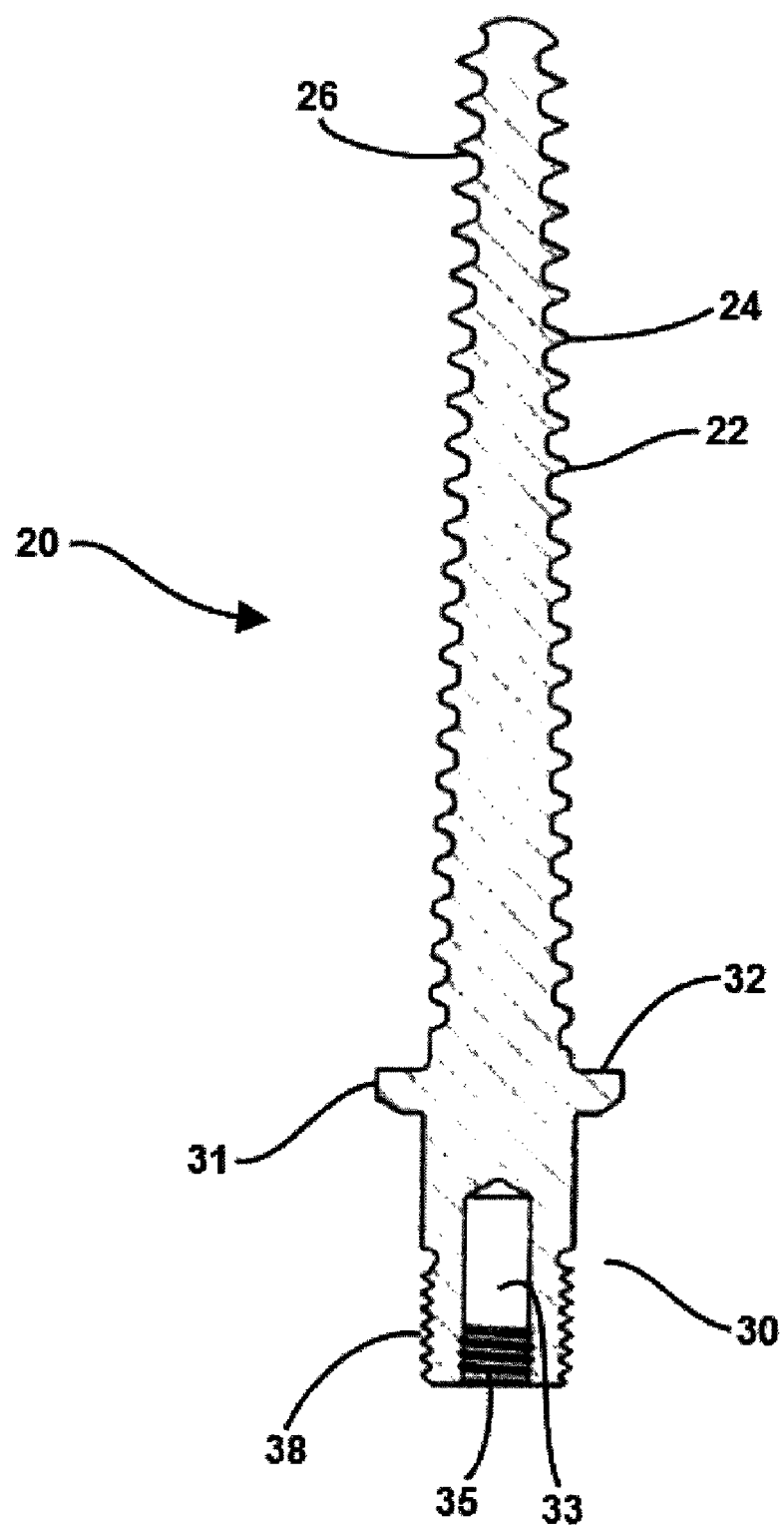
FIG. 3B is a cross-sectional view of the pedicle screw of FIG. 3A.

Referring to FIGS. 3A and 3B, each pedicle screw 20 has a bone engaging shank 22 on the distal portion 28 of the screw. The outer surface 24 of the shank may include one or more bone engagement mechanisms to facilitate gripping engagement of the pedicle screw to the bone. In the illustrated embodiment, for example, the outer surface 24 defines an external thread 26 that extends along at least a portion of the bone-engaging shank 22. Optionally, the external thread can extend along substantially the elongate length of the engaging shank 22. In another aspect, it is contemplated that the bone engaging shank of the pedicle screw can be tapered such that the shank diameter of the bone engaging shank (i.e., the major diameter of the external thread 26) can decrease as the thread approached the distal end of the pedicle screw. In the illustrated example, the pedicle screw has a distal threaded portion (i.e., external thread 26) that is configured to engage bone of a subject, such as, the subject's spinal column. One skilled in the art will appreciate that bone engagement mechanisms other than external thread 26 may be employed, including, for example and without limitation, one or more annular ridges, multiple threads, dual lead treads, variable pitched threads, and/or any other conventional bone engagement mechanism.

Further, each pedicle screw 20 has a proximal portion 30 that defines an external drive feature 31 that abuts the bone engaging shank 22 of the pedicle screw. It is contemplated that the external drive feature 31 can be configured for complementary receipt of a drive tool 110, for example, the exemplified wrench tool described below, such that the external drive feature can be selectively coupled with the drive tool so that the pedicle screw can be selectively driven into the subject's bone. In one aspect, the pedicle screw 20 is driven until a bottom shoulder surface 32 of the external drive feature, which extends radially outwardly beyond the major diameter of the bone engaging shank of the pedicle screw, is positioned in contact with the bone.

The proximal portion 30 of the pedicle screw further defines a head 34 that is configured to fit within a portion of the drive tool. For example, the head 34 can be generally cylindrical in shape and extend outwardly along the longitudinal axis of the pedicle screw. Further, it is contemplated that the proximal end portion 36 of the head of the pedicle screw can define an external thread 38 that extends along at least a portion of the proximal end portion of the head 34 and that is configured to complementarily engage a fastener 100, such as the fastener exemplified in FIG. 6, that defines an aperture therethrough.

Still further, the head of the pedicle screw can define a threaded cavity 33 that extends inwardly substantially along the longitudinal axis of the pedicle screw and further defines an internal thread 35 that extends along at least a portion of the proximal end cavity and that is configured to complementarily engage a distal threaded portion 86 of an extension rod 80.

Figure 4A:
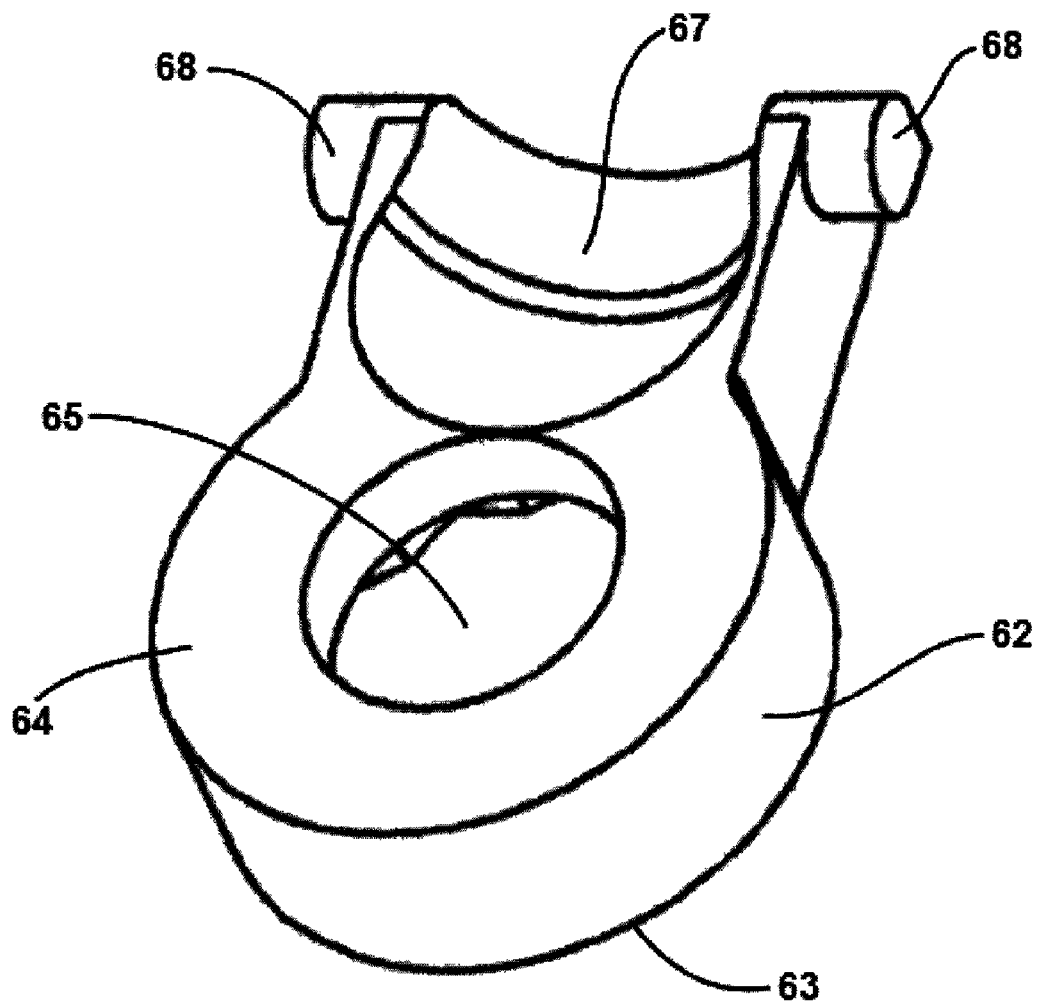
FIG. 4A is a perspective view of an exemplary embodiment of a distal body portion of a coupling member for the spinal stabilization system of the present invention.
Figure 4B:
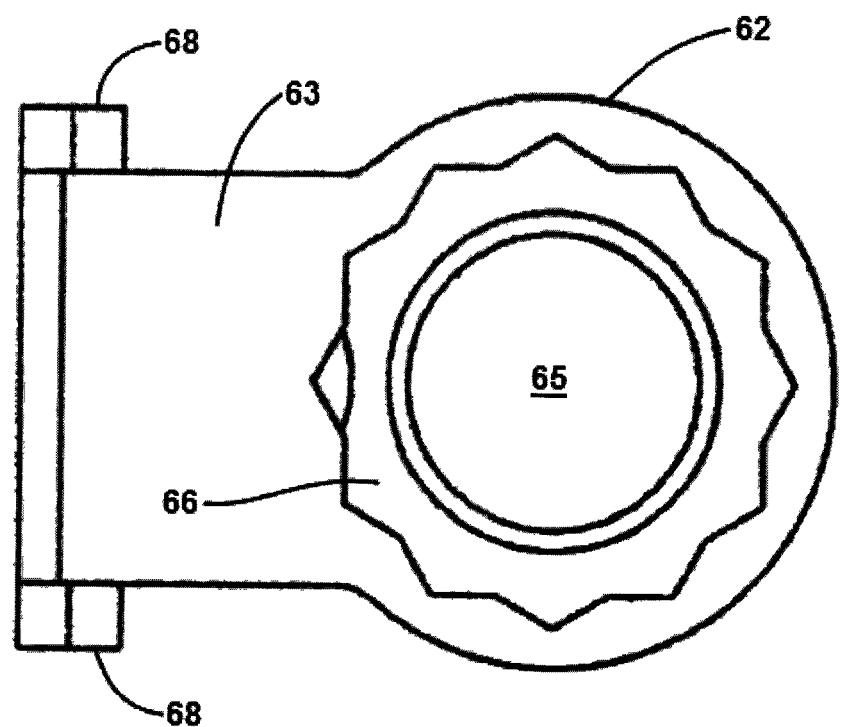
FIG. 4B is a bottom elevation view of the distal body portion of FIG. 4A.
Figure 4C:
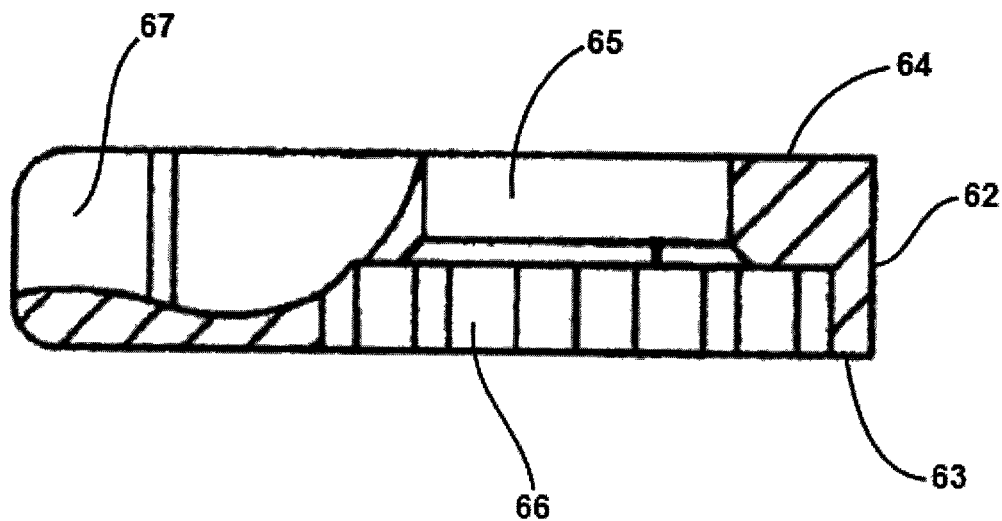
FIG. 4C is a cross-sectional view of the distal body portion of FIG. 4B.

Each coupling member 60 is configured to engage the proximal portion of the pedicle screw. In one aspect, each coupling member comprises a distal body portion 62 and a proximal body portion 70 that are configured to be selectively and hingeably connected to operatively define the socket portion of the coupling member. Referring to FIGS. 4A-C, the distal body portion comprises a lower surface 63, an opposed upper surface 64, and an aperture 65 extending therethrough. In one aspect, the lower surface 63 defines a trough 66 that circumferentially surrounds the aperture. In this aspect, the trough can have a peripheral shape that is complementary to the peripheral shape of the external drive feature 31 of the pedicle screw so that, when operatively coupled, the distal body portion 62 of the coupling member 60 can be fixed with respect to the proximal portion 30 of the pedicle screw.

The upper surface of the distal body portion 62 defines a seat 67 extending inwardly from an edge of the distal body portion toward the aperture 65. In one aspect, at least a portion of the seat 67 may have surface texturing, knurling, and/or ridges. In another aspect, the distal body portion 62 defines a pair of opposing pins 68 that extend outwardly from opposing sides of the distal body portion.

Figure 5A:
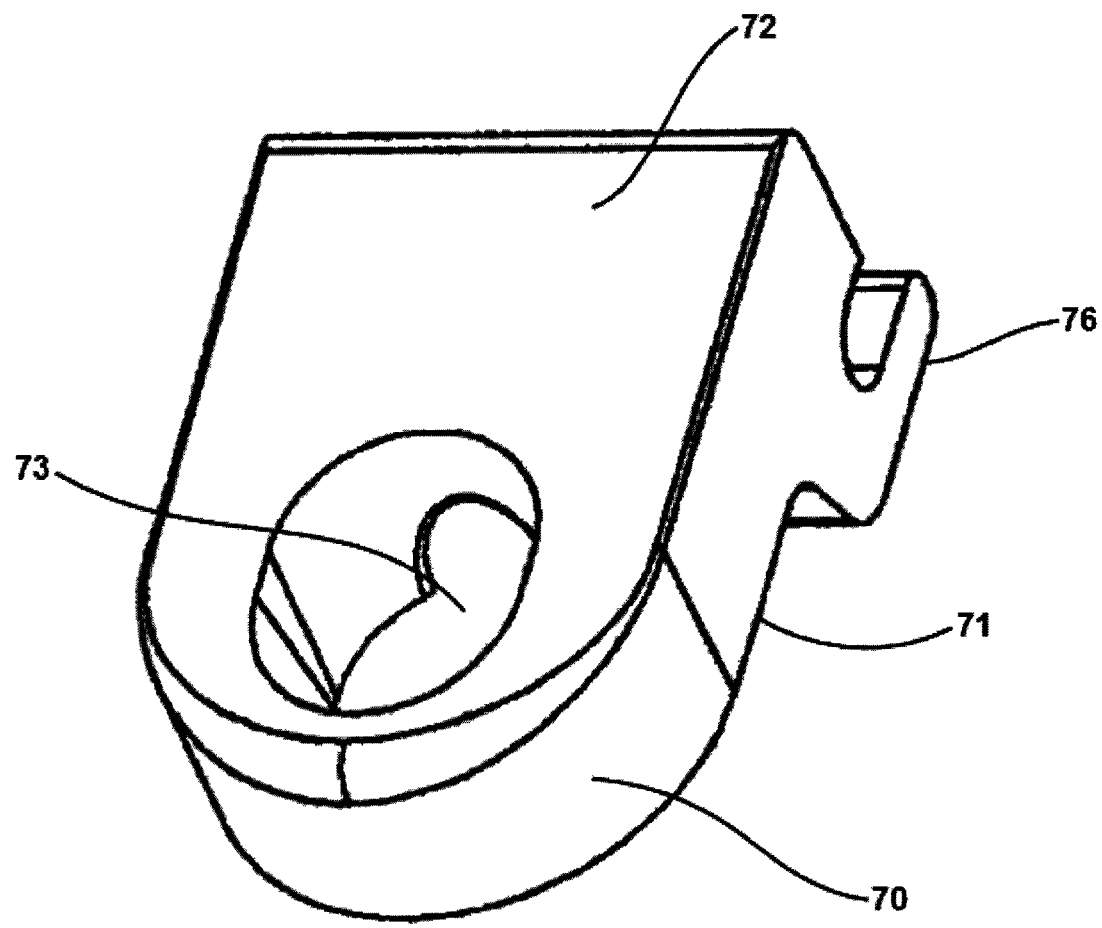
FIG. 5A is a perspective view of an exemplary embodiment of a proximal body portion of a coupling member for the spinal stabilization system of the present invention.
Figure 5B:
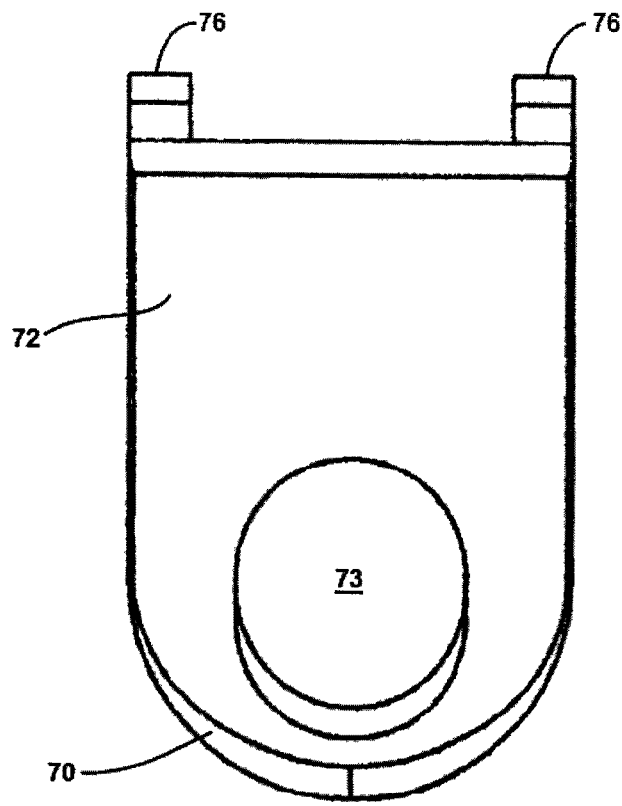
FIG. 5B is a top elevation view of the proximal body portion of FIG. 5A.
Figure 5C:
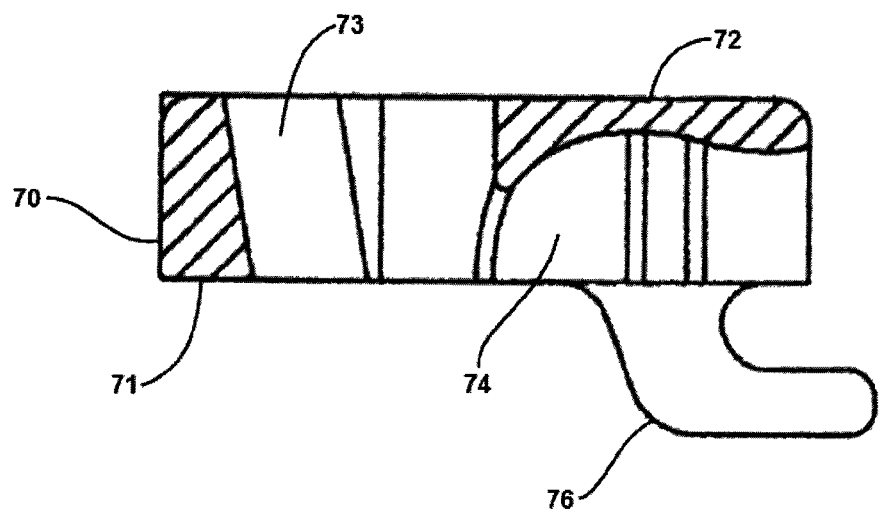
FIG. 5C is a cross-sectional view of the proximal body portion of FIG. 5B.

Referring to FIGS. 5A-C, the proximal body portion 70 of the coupling member 60 comprises a bottom surface 71, an opposed top surface 72, and an aperture 73 extending therethrough. It will be appreciate that aperture 65 of the distal body portion and aperture 73 of the proximal body portion form a common coupling aperture for the coupling member 60 when the respective proximal and distal body portions are hingeably connected. In one aspect, the bottom surface 71 defines a seat 74 that extends inwardly from an edge of the proximal body portion toward the aperture 73. In one aspect, at least a portion of the seat 74 may have surface texturing, knurling, and/or ridges. In another aspect, the bottom surface 71 of the proximal body portion can define a pair of opposed hook members 76 that extend beyond the peripheral edge of the proximal body portion to either side of and substantially parallel to the portion of the seat 74 that extend inwardly from the edge of the proximal body portion. As one skilled in the art will appreciate, the opposed hook members 76 are configured to hingeably connect to the pair of opposing pins 68 that extend outwardly from opposing sides of the distal body portion.

In one aspect, when the respective proximal and distal portions 70, 62 of the coupling member 60 are hingeably connected the respective seats 67, 74 are positioned in substantial opposition and define a socket portion of the coupling member that is configured to receive a socket engaging portion 42 of the rod clamp 40 such that the engaged coupling member and pedicle screw 20 can be pivoted three-dimensionally relative to the respective rod clamp 40. Thus, in the illustrated embodiment, each coupling member is configured to engage a proximal portion of a pedicle screw. Further, each coupling member 60 comprising a socket portion 69 that is configured to receive the socket engaging portion of a rod clamp.

Figure 7:
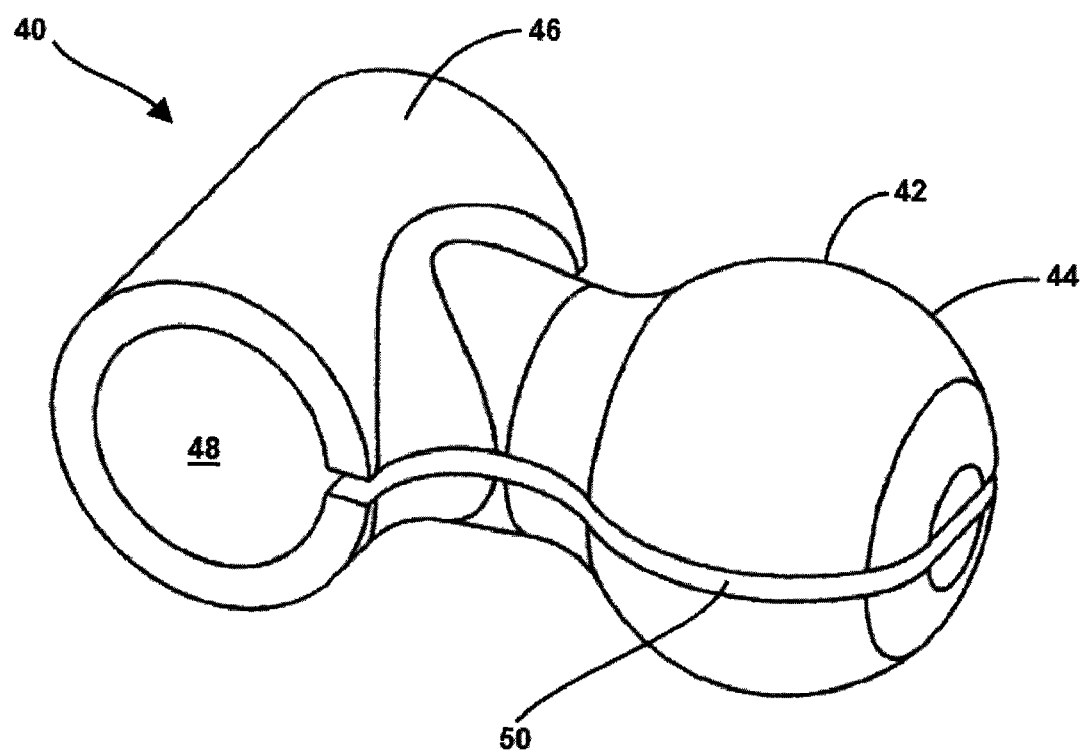
FIG. 7 is a perspective view of a rod clamp for the spinal stabilization system of the present invention.

Referring now to FIG. 7, the rod clamp 40 can exemplarily comprise a head 44 formed at the socket engaging portion 42 of the rod clamp and a mounting portion 46 positioned substantially transverse to the longitudinal axis of the socket engaging portion. In one aspect, at least portions of the socket engaging portions of the rod clamp can be generally spherical in shape to facilitate pivoting of the rod clamp relative to the coupling member. In another aspect, at least a portion of the head 44 may have surface texturing, knurling, and/or ridges. In yet another aspect, the mounting portion 46 of the rod clamp defines a substantially cylindrical aperture 48 that extends substantially transverse to the longitudinal axis of the socket engaging portion and that is configured for receiving the support rod 12 therethrough.

Further, the socket engaging portion 42 of the rod clamp defines a slit 50 that that substantially bisects the head and that is in communication with the aperture of the mounting portion of the rod clamp. In one aspect, the slit 50 extends in a plane that substantially bisects the longitudinal axis of the aperture 48 of the mounting portion. One skilled in the art will appreciate that the slit 50 allows the socket engaging portion 42 to be operatively movable between two effective diameters, a larger effective uncompressed diameter and a smaller effected compressed diameter. One skilled in the art will also appreciate that the effective diameter of the aperture 48 of the mounting portion 46 is reduced when the effective diameter of the socket engaging portion is reduced, i.e., when the socket engaging portion is compressed due to the application of a compressive force. In use, when the effective diameter of the aperture 48 of the mounting portion is reduced, the rod clamp 40 can be selectively secured in position relative to the coupling member 60 and the support rod 12. Thus, in use, it is contemplated that the rod mounting portion of the rod clamp can be selectively adjustable between a first configuration, which allows slidable movement of the support rod through the aperture, and a second clamped configuration, in which the rod clamp can be fixed at a predetermined position along the support rod.

Figure 8:
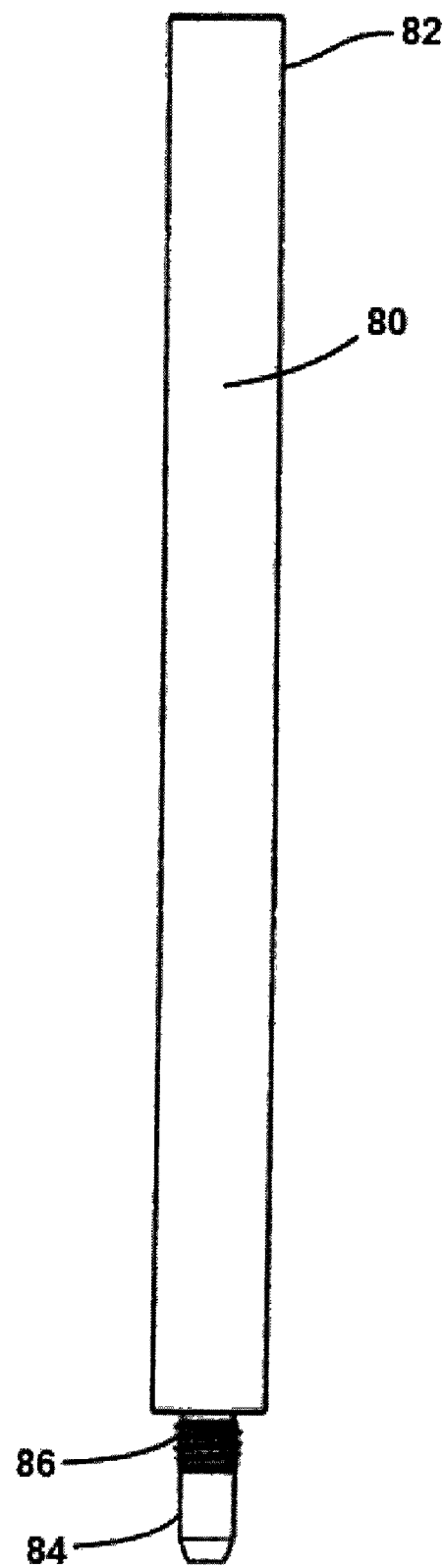
FIG. 8 is a side elevational view of an extension rod for the spinal stabilization system of the present invention.

Referring now to FIG. 8, an extension rod 80 is shown having a proximal end 82 and a distal end 84. In this aspect, it is contemplated that a portion of the distal end will define a distal treaded portion 86 that is configured for operative attachment and selective receipt within the threaded cavity 33 therein the head of the pedicle screw. As shown in FIG. 2, when selectively mounted thereto the head of the pedicle screw, the extension rod extends substantially co-axial to the longitudinal axis of the pedicle screw. As one will appreciate and will be explained in more detail below, the extension rod is selectively removed after the coupling member is fixed relative to the pedicle screw and the rod clamp.

In use, the common aperture of the hingedly connected distal and proximal body portions of the coupling member 40 is configured to be received onto the outer diameter of the extension rod 80 such that the coupling member 40 can be slidably moved along the extension rod 80 for operative positioning about the proximal end of the pedicle screw 20.

Figure 6:
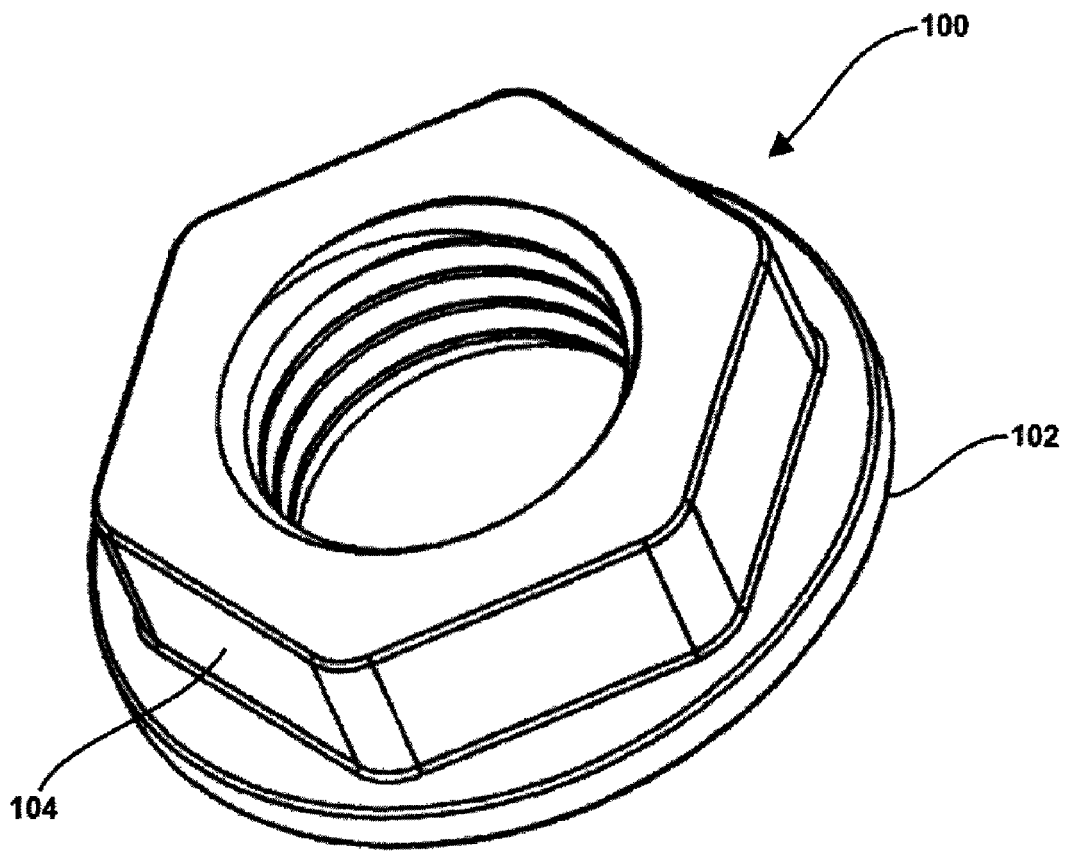
FIG. 6 is a perspective view of a fastener for the spinal stabilization system of the present invention.

In one aspect, the fastener 100 exemplarily shown in FIG. 6 can comprise a plurality of fasteners, such as, for example and without limitation, nut members 102 that have an external drive feature 104 that is configured to be selectively coupled with the drive tool so that the nut member can be selectively driven down the external thread 38 of the head 34 of the pedicle screw. Thus, in operation, each fastener 100 can be slidably moved along a respective extension rod 80 for operative mounting thereto the proximal end of the pedicle screw to which the extension rod is operatively coupled. One would appreciate, as shown in FIG. 2, that it is contemplated that the distal and proximal body portion of the coupling member would be mounted onto the head of the pedicle screw between the fastener and top shoulder surface 33 of the external drive feature of the proximal portion of the pedicle screw 20. In this fashion, as the fastener is driven down the external thread 38 of the head 34 of the pedicle screw into contact with the upper surface of the proximal body portion, the respective proximal and distal body portion of the coupling member are drawn toward each other which effects a reduction in the effective diameter of the socket portion of the coupling member. As one skilled in the art will appreciate, the reduction of the effective diameter of the socket portion of the coupling member exerts pressure onto the socket engaging portion of the rod clamp and effects movement of the mounting portion of the rod clamp from the first configuration towards the second clamped configuration. When the rod clamp is in the second clamped configuration, the rod clamp is fixed relative to the support rod, the coupling member and the pedicle screw.

Of course, if the fastener 100 is backed off, the force acting on the rod clamp will be relaxed and the socket engaging portion of the rod clamp will bias back toward the first relaxed configuration such that the rod clamp can be moved relative to the support rod, the coupling member and the pedicle screw. In a further aspect, it will be appreciated that the support rod can be operatively position as any desired position relative to the pedicle screw. In one exemplary aspect, and not meant to be limiting, the support rod can be operatively positioned in a plane that is offset to a side of the longitudinal plane of the plurality of pedicle screws.

Figure 9:
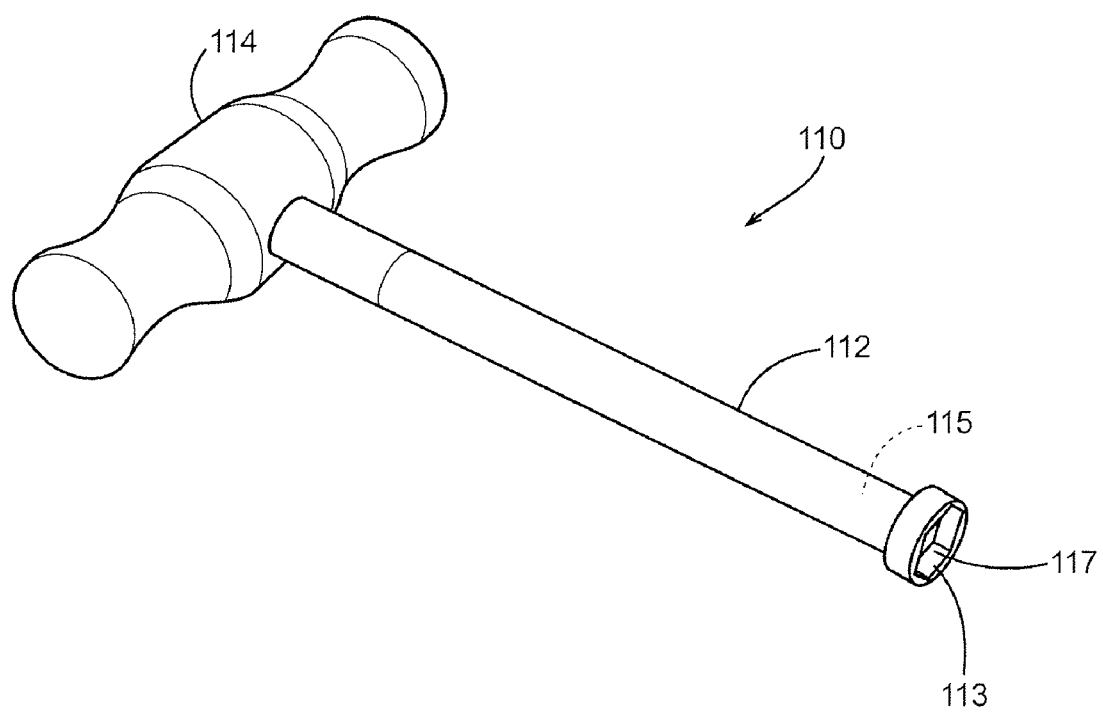
FIG. 9 is a perspective view of a drive tool for the spinal stabilization system of the present invention.
Figure 10:
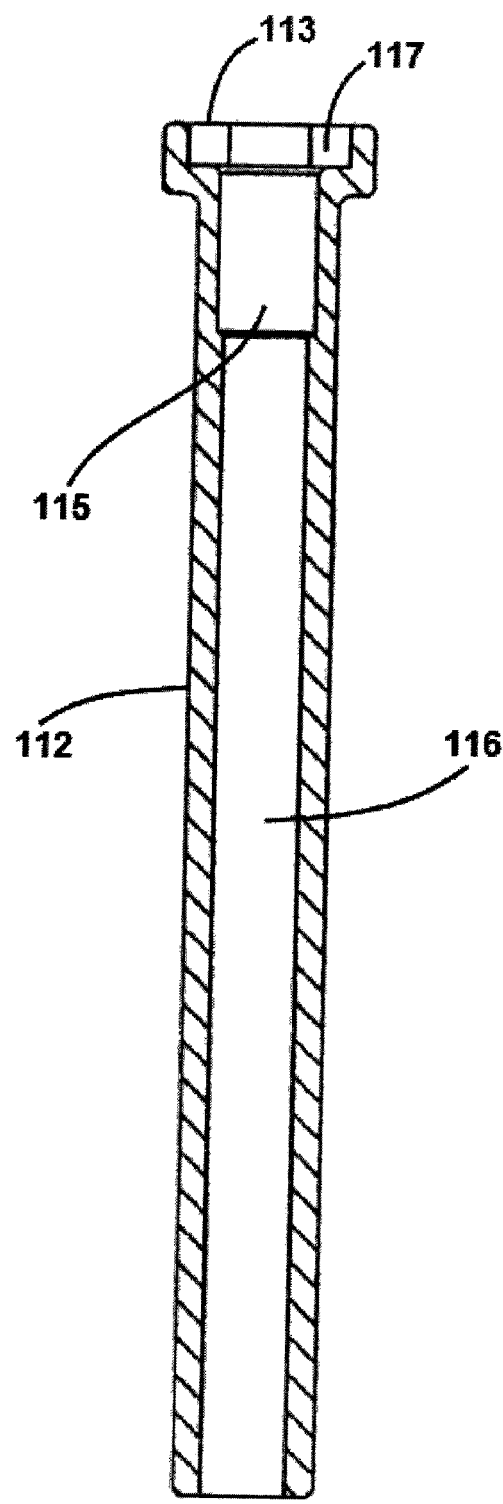
FIG. 10 is a partial cross-sectional view of the drive tool of FIG. 11.

In a further aspect, the spinal stabilization system of the present invention can further comprise a drive tool 110 and/or a stabilizer tool 120. Referring first to FIGS. 9 and 10, the drive tool can comprise an elongate shaft 112 coupled to a hand grip 114 that can be configured for applying a rotative force. In one aspect, the elongate shaft 112 has a hollow bore 116 that extends inwardly from an open distal end 113 of the drive tool and is configured to receive at least a portion of the extension rod therein. As exemplified in the figures, a distal end portion 15 of the hollow bore is configured for receipt thereon the proximal portion of the pedicle screw 20 and has a drive surface 117 that is adapted to operatively engage the external driving feature of the pedicle screw so that the pedicle screw can be driven into the bone. Further, one will appreciate that the distal end portion 15 of the hollow bore is also configured to operatively engage the fastener 100 so that the fastener can be driven down to effect compression of the respective proximal and distal portions of the coupling member.

Figure 11:
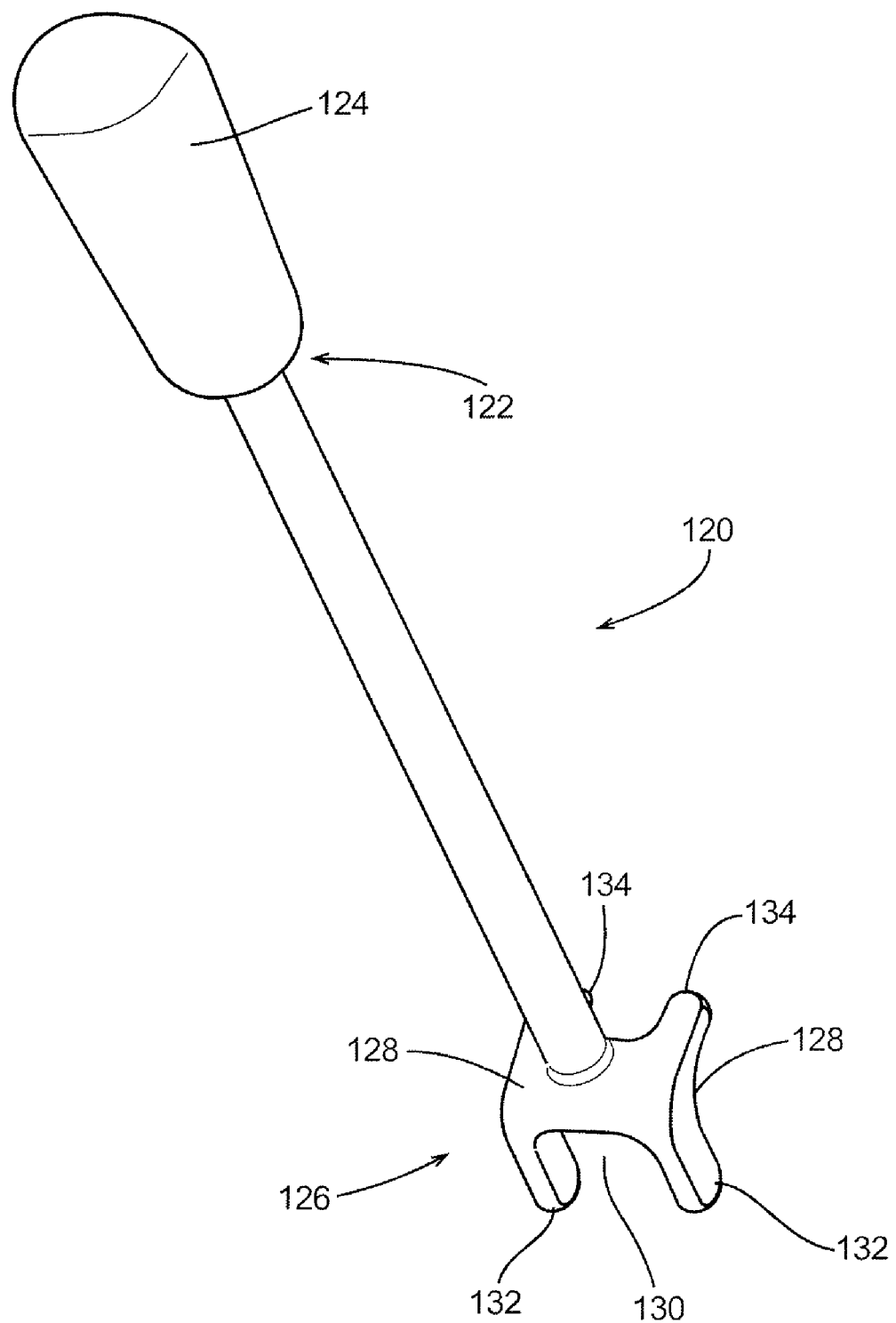
FIG. 11 is a perspective view of a stabilizer tool for the spinal stabilization system of the present invention.
Figure 12:
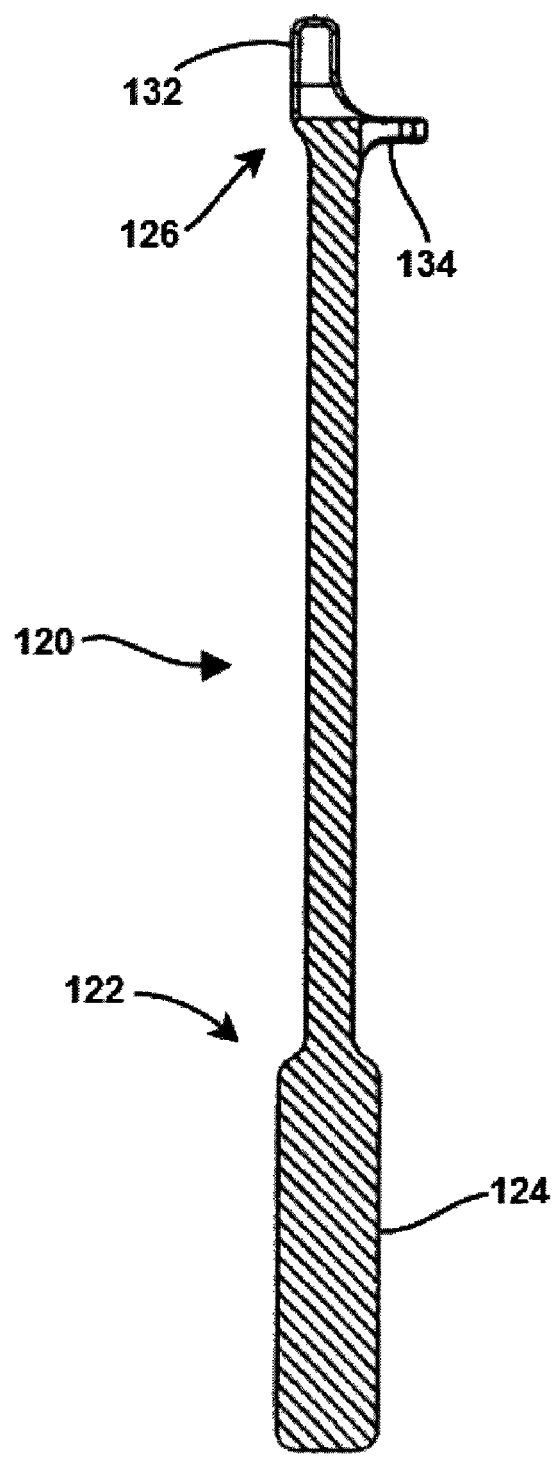
FIG. 12 is a cross-sectional view of the stabilizer tool of FIG. 9.
Figure 13A:
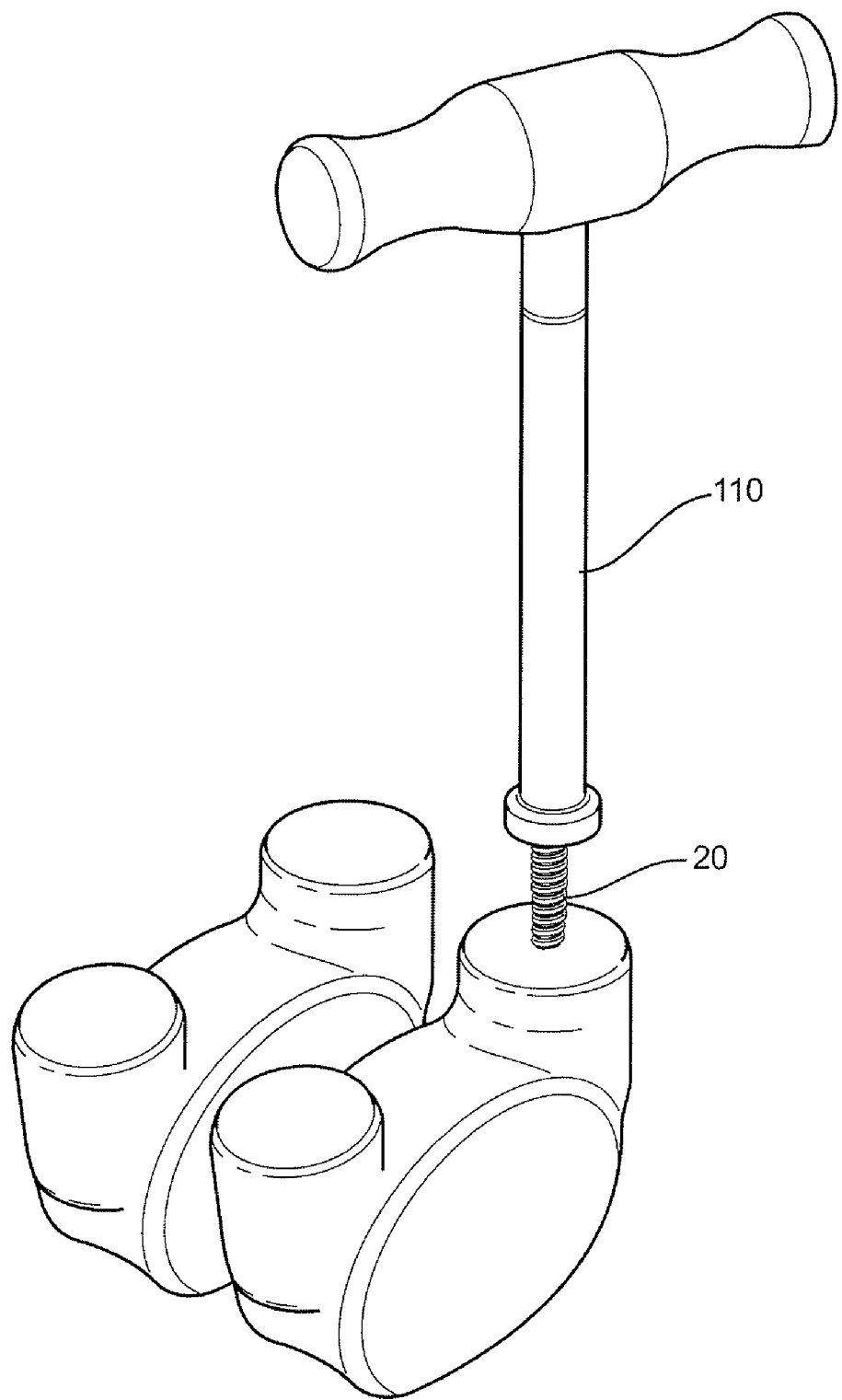
FIGS. 13A-H are perspective views of an exemplary method of minimally invasively using the spinal stabilization system of the present invention to stabilize a portion of a patient's spine.
Figure 13B:
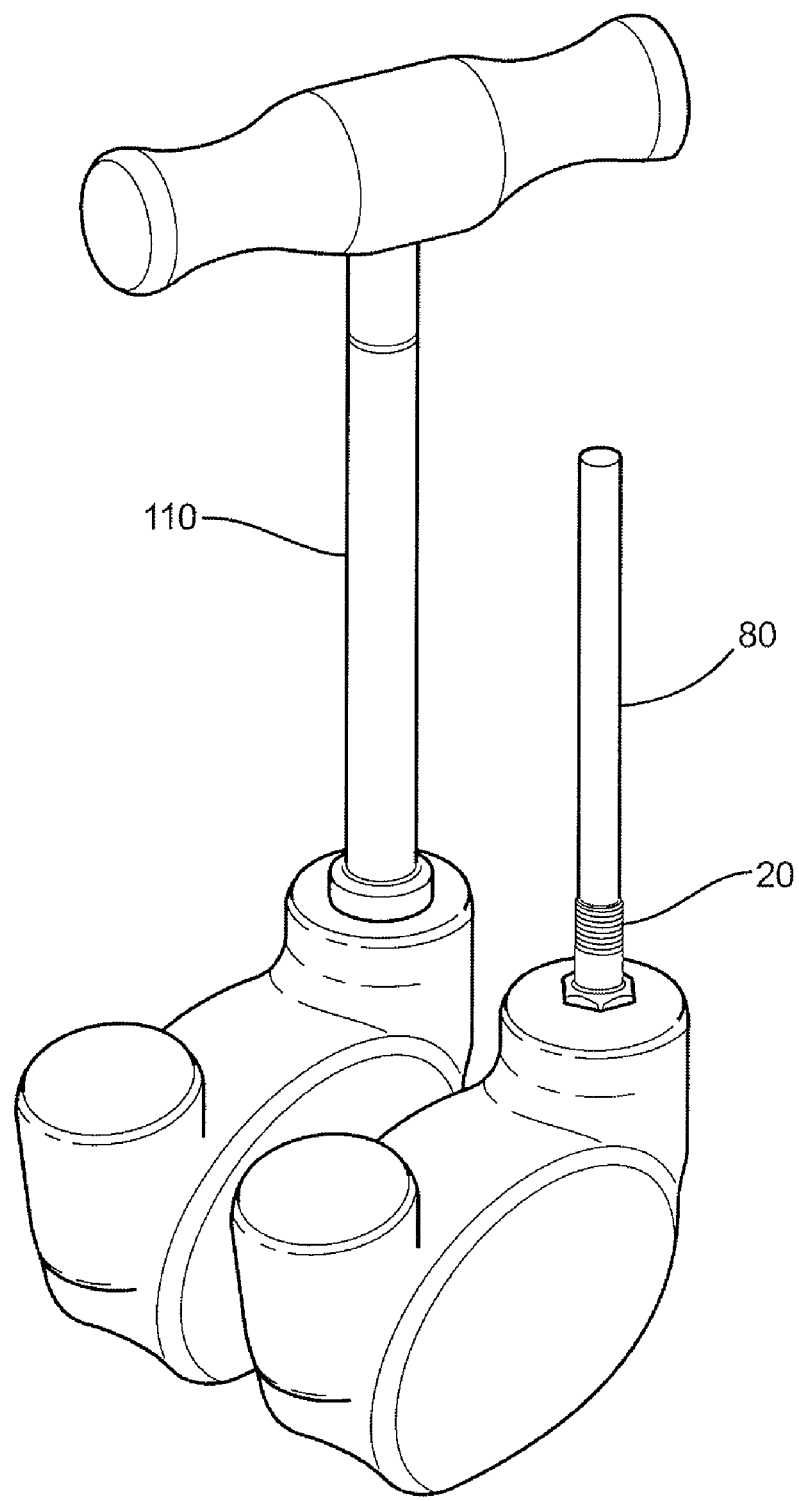
Figure 13C:
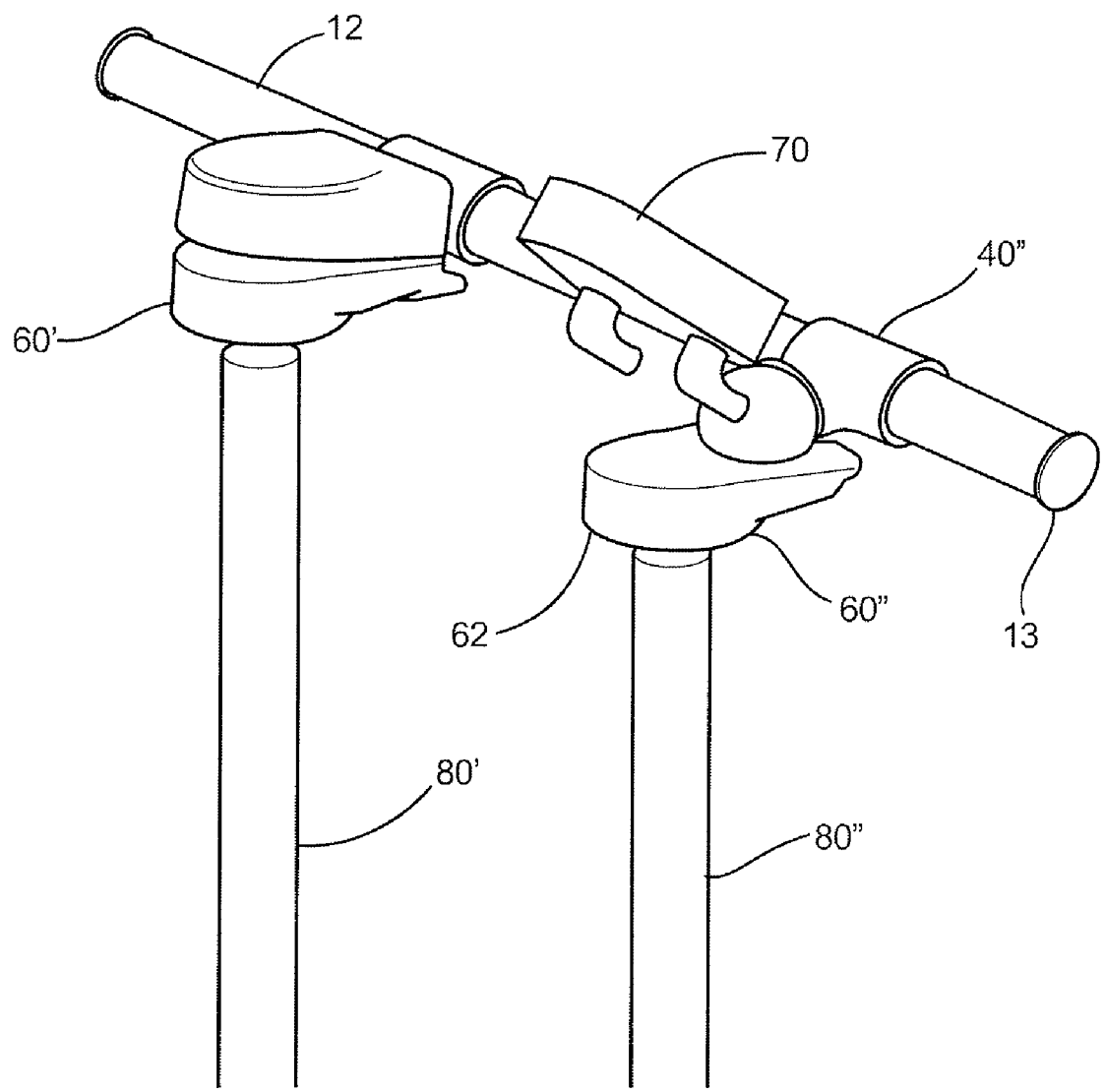
Figure 13D:
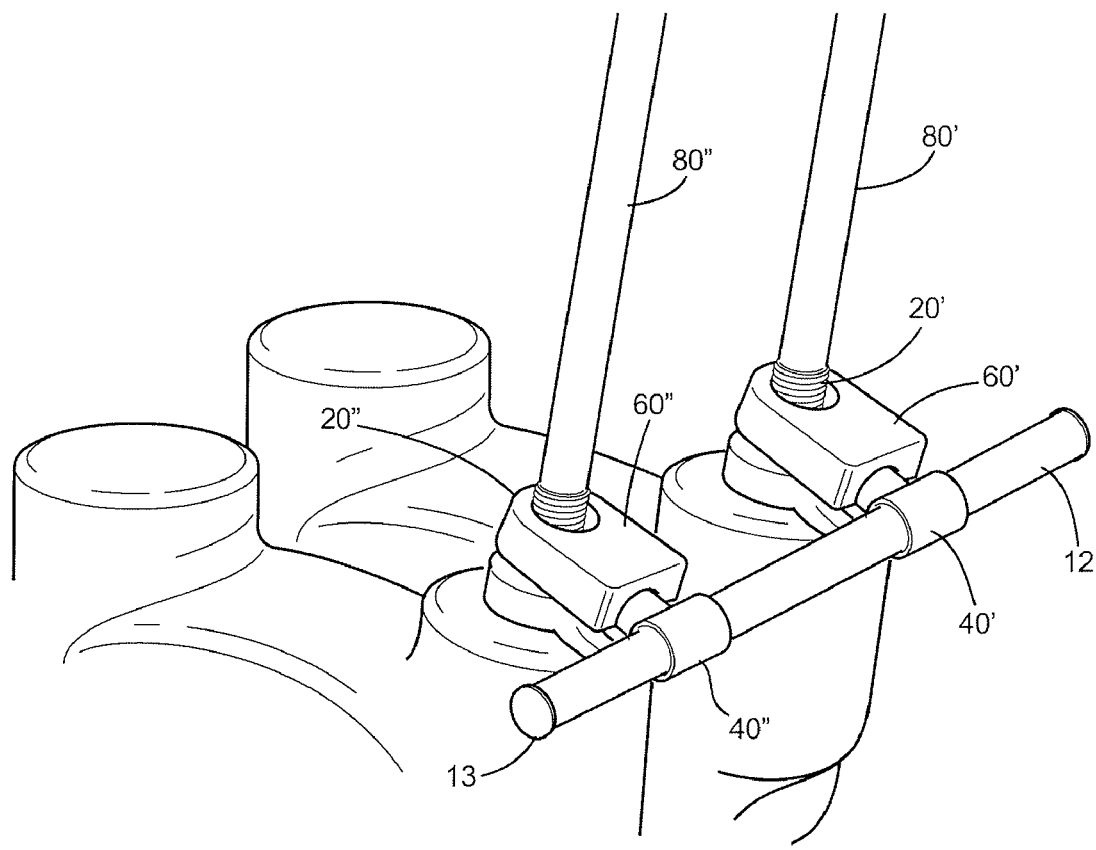
Figure 13E:
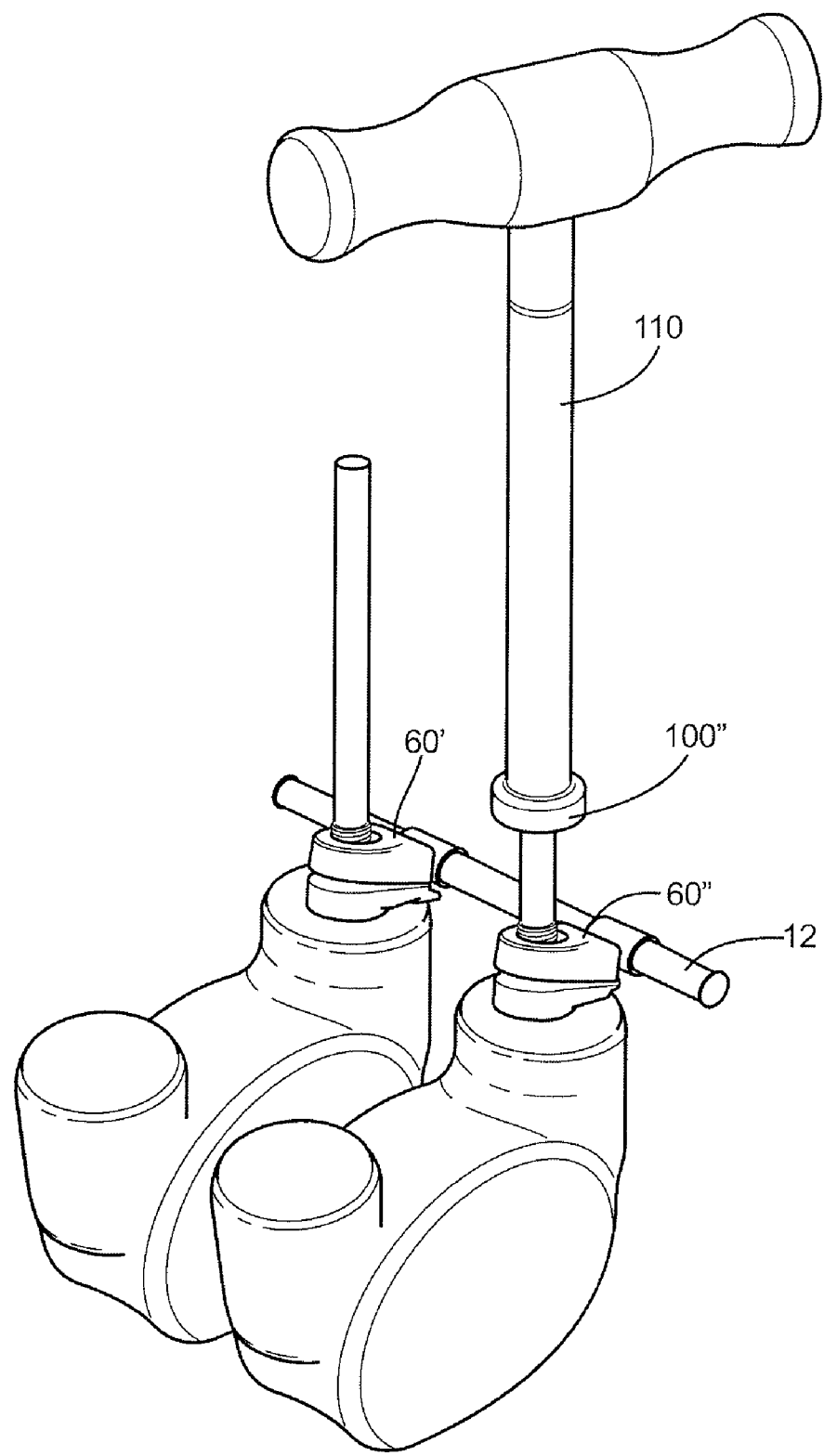
Figure 13F:
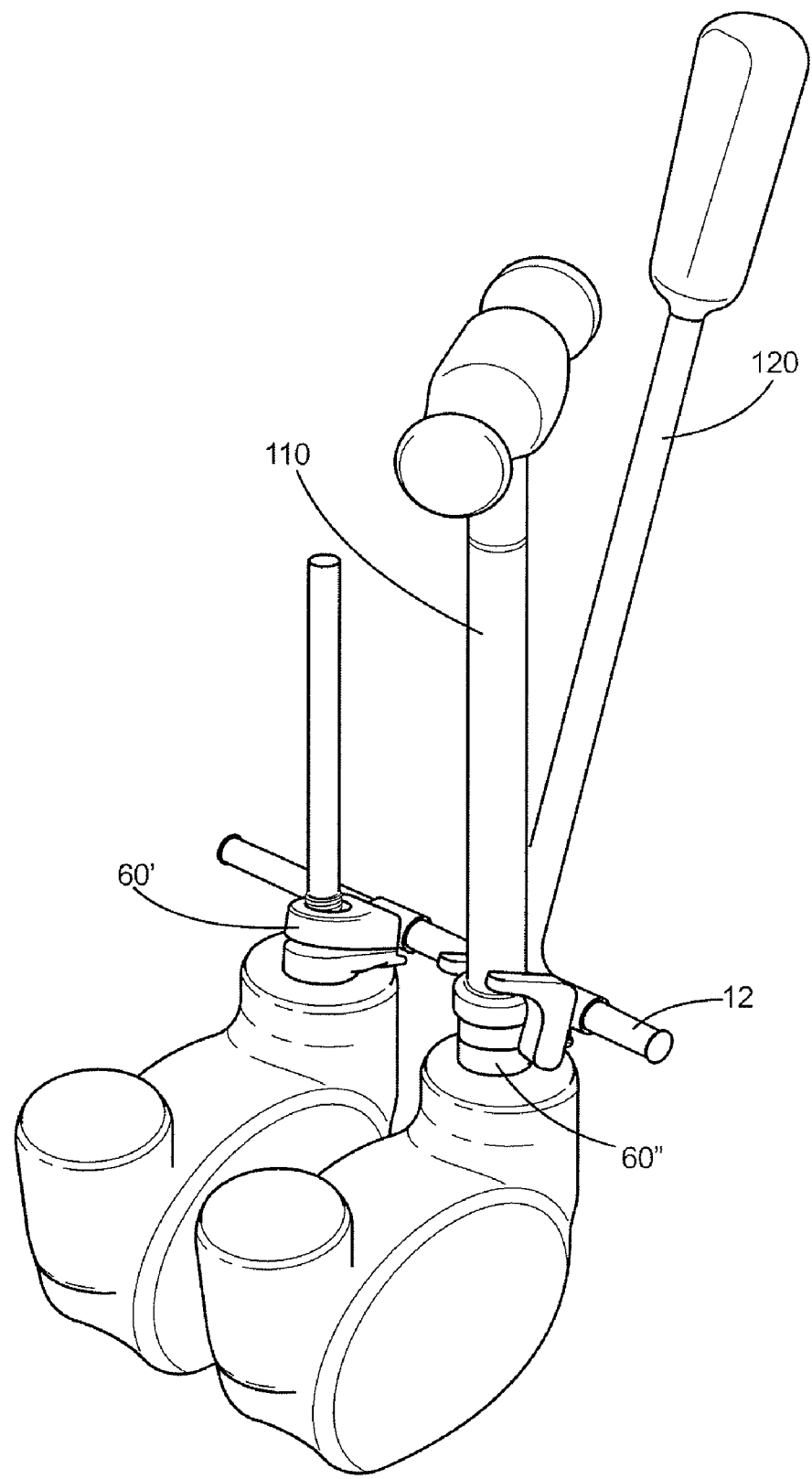
Figure 13G:
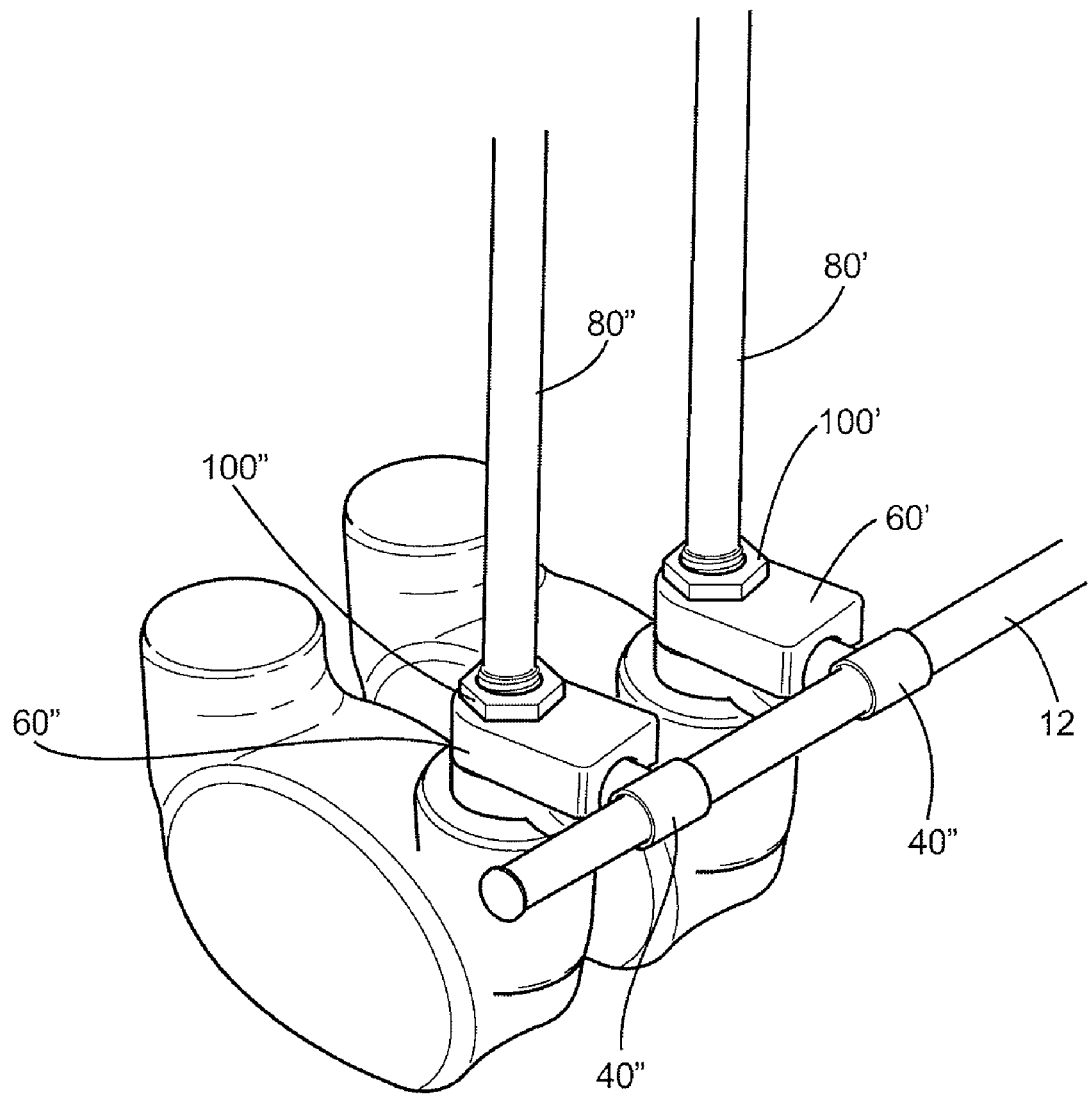
Figure 13H:
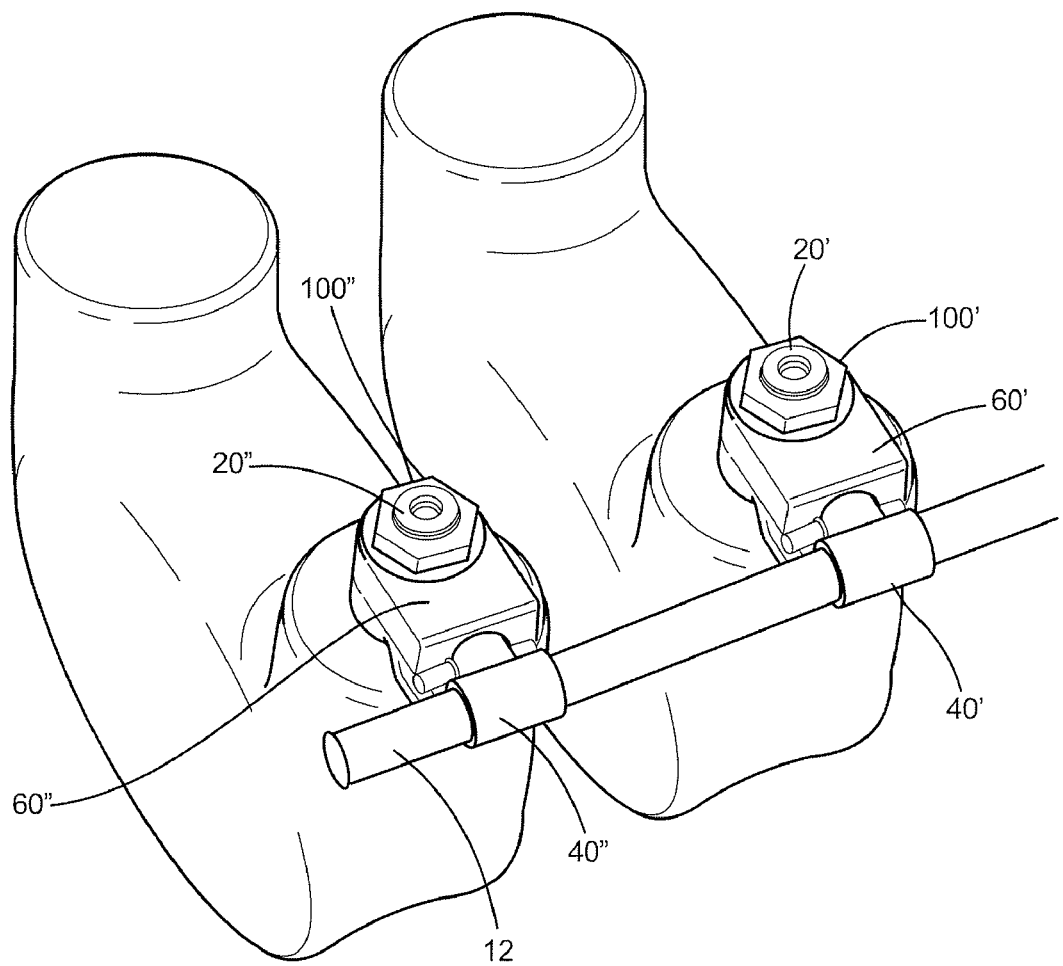

Referring now to FIGS. 11 and 12, the stabilizer tool 120 can have a proximal end portion 122 having a grip surface 124 configured to be grasped by the surgeon and a distal end portion 126 that defines a pair of spaced L-shaped members 128 that define an interior volume 130. In one aspect, a first pair of opposed legs 132 of the L-shaped members extend outwardly generally parallel to the longitudinal axis of the stabilizer tool and a second pair of opposed legs 134 of the L-shaped members extend outwardly generally transverse to the longitudinal axis of the stabilizer tool. In use, the stabilizer tool can be positioned such that the second pair of opposed legs can be positioned to exert pressure upon the external surface of the drive tool 110 proximate the distal end of the drive tool and concurrently the first pair of opposed legs 132 is positioned about a portion of the proximal body portion of the coupling member to substantially fix the position of the coupling member as the fastener is driven down. In this aspect, the portion of the proximal body portion of the coupling member is positioned therein the interior volume 130 of the stabilizer tool.

In one exemplary method of using the spine stabilization system of the present invention comprises initially prepping and draping the surgical site. One exemplary approach, and not meant to be limiting, uses a posterior lateral approach that may substantially comprise a Wiltse approach. In this aspect, a muscle-splitting finger dissection approach can be used to gain access to the desired anatomical location in the spine, which are generally adjacent the pedicles of the vertebra of interest. Once the pedicles are exposed, they can be conventionally prepped.

Next, a plurality of pedicle screws can be driven therein predetermined locations along a subject's spinal column with the drive tool. In one aspect, it is contemplated that the insertion of the pedicle screws can be guided and/or monitored by fluoroscopy or other conventional imaging techniques. It is further contemplated that a conventional awl can be used to form alignment bores in the bones prior to the insertion and driving of the pedicle screws thereinto the bone.

Subsequently, the distal end of an extension rod is connected to the interior cavity of the proximal portion of each of the pedicle screws. When mounted in this fashion, the proximal end portion of each extension rod extends posterior to the skin of the subject.

Next, a plurality of rod clamps are mounted thereon the elongated support rod. The plurality of coupling members is hingeably mounted about a portion of the rod clamps, i.e., the socket engaging portion of each rod clamp is mounted therein a respective socket portion of each coupling member, and the common apertures of the proximal and distal body portion of the coupling member are slidably mounted onto the proximal ends of the plurality of extension rods. Next, the plurality of coupling members are slid down the extension rods and into the body until the coupling members are operatively engaged therewith the exterior drive surface of the proximal portions of the pedicle screws.

A plurality of fasteners can then be slideably mounted onto the proximal ends of the plurality of extension rods and slid down the respective extension rods into contact with the threaded portions of the heads of the pedicle screws. If desired, the stabilizer tool can be positioned to stabilize the relative positions of the coupling members and rod clamps as each fastener is selectively driven with the drive tool about the proximal portion of the pedicle screw and against portions of the coupling member such that the respective rod clamp can be fixed at a predetermined positions along the support rod. Subsequently, after all the fasteners are secured, the plurality of extension rods can be removed from the plurality of pedicle screws.

What is claimed is:

1. A spine stabilization system, comprising:
    a first and second pedicle screw, each pedicle screw comprising a distal threaded portion configured to engage bone of a subject's spinal column;
    a rigid elongated support rod;
    a first rod clamp having a rod mounting portion configured for mounting thereto a portion of the support rod and a socket engaging portion;
    a second rod clamp having a rod mounting portion configured for mounting thereto a portion of the support rod and a socket engaging portion;
    a first coupling member configured to engage a proximal portion of the first pedicle screw and further comprising a socket portion configured to receive the socket engaging portion of the first rod clamp such that the first coupling member and first pedicle screw can be pivoted three-dimensionally relative to the first rod clamp and support rod;
    a second coupling member configured to engage a proximal portion of the second pedicle screw and further comprising a socket portion configured to receive the socket engaging portion of the second rod clamp such that the second coupling member and second pedicle screw can be pivoted three-dimensionally relative to the second rod clamp and support rod; and
    a first extension rod configured for operative attachment to a proximal portion of the first pedicle screw,
    wherein the proximal end of the first pedicle screw comprises a threaded cavity and the first extension rod comprises a distal threaded portion that is complementary to the threaded cavity such that the threaded cavity of the first pedicle screw is configured to receive the distal threaded portion of the first extension rod.

2. The system of claim 1, wherein the rod mounting portion of the first rod clamp defines an aperture for receiving the support rod therethrough, and wherein the rod mounting portion is selectively adjustable between a first configuration allowing slidable movement of the support rod through the aperture and a second clamped configuration wherein the first rod clamp can be fixed at a predetermined position along the support rod and is fixed relative to the support rod, the first coupling member and the first pedicle screw.

3. The system of claim 1, wherein the rod mounting portion of the second rod clamp defines an aperture for receiving the support rod therethrough, and wherein the rod mounting portion is selectively adjustable between a first configuration allowing slidable movement of the support rod through the aperture and a second clamped configuration wherein the second rod clamp can be fixed at a predetermined position along the support rod and is fixed relative to the support rod, the second coupling member and the second pedicle screw.

4. The system of claim 1, wherein the first pedicle screw is operatively configured for placement within a first vertebral body and wherein the second pedicle screw is operatively configured for placement within a second vertebral body such that support rod operatively spans the intervertebral space between the first and second vertebrae.

5. The system of claim 1, wherein the socket engaging portions of the first and second rod clamps are generally spherical in shape to facilitate pivoting of the rod clamp relative to the respective first and second coupling members.

6. The system of claim 1, further comprising a second extension rod configured for operative attachment to a proximal portion of the second pedicle screw.

7. The system of claim 6, wherein the proximal end of the second pedicle screw comprises a threaded cavity and the second extension rod comprises a distal threaded portion that is complementary to the threaded cavity such that the threaded cavity of the second pedicle screw is configured to receive the distal threaded portion of the second extension rod.

8. The system of claim 7, wherein the first and second extension rods are selectively removable from the first and second pedicle screws.

9. The system of claim 7, wherein the first coupling member defines an aperture for receiving the first extension rod therethrough and wherein the first coupling member can be slidably moved along the first extension rod for operative positioning about the proximal end of the first pedicle screw.

10. The system of claim 9, wherein the second coupling member defines an aperture for receiving the second extension rod therethrough and wherein the second coupling member can be slidably moved along the second extension rod for operative positioning about the proximal end of the second pedicle screw.

11. The system of claim 10, wherein the first and second coupling members each comprise a distal body portion and a proximal body portion, wherein the distal and proximal body portions are hingeably connected to operatively define the first and second socket portions.

12. The system of claim 11, wherein the distal and proximal body portions each define apertures for receiving the first and second support rods therethrough and wherein the first and second coupling members can be slidably moved along the first and second extension rods for operative positioning about the proximal end of the first and second pedicle screws.

13. The system of claim 12, further comprising first and second nut members each defining an aperture therethrough, wherein the first and second nut members can be slidably moved along the first and second extension rods respectively for operative positioning about the proximal end of the first and second pedicle screws.

14. The system of claim 13, wherein the proximal ends of the first and second pedicle screws each comprise threaded portions for complementary engagement with the first and second nut members.

15. The system of claim 14, wherein the first and second nut members can be tightened against the proximal body portions to adjust the first and second rod clamps into their second clamped configuration.

16. The system of claim 14, wherein the first and second nut members can be loosened to adjust the first and second rod clamps into their first configuration allowing slidable movement of the rod claims along the support rod.

17. The system of claim 1, wherein the support rod is operatively positioned in a plane offset to a side of the longitudinal plane of the first or second pedicle screw.

18. A spine stabilization system, comprising:
a plurality of pedicle screws, each pedicle screw configured to engage bone of a subject's spinal column;
a plurality of rod clamps, each rod clamp having a socket engaging portion;
a plurality of coupling members, each coupling member configured to engage a proximal portion of a pedicle screw and further comprising a socket portion configured to receive the socket engaging portion of a rod clamp such that the engaged coupling member and pedicle screw can be pivoted three-dimensionally relative to the respective rod clamp;
an elongated support rod, wherein each rod clamp has a rod mounting portion that defines an aperture for receiving the support rod therethrough, and wherein the rod mounting portion is selectively adjustable between a first configuration allowing slidable movement of the support rod through the aperture and a second clamped configuration wherein the rod clamp can be fixed at a predetermined position along the support rod;
a plurality of extension rods, each extension rod being configured for operative attachment to the proximal portion of a pedicle screw, wherein the proximal end of the pedicle screw defines a threaded cavity that is configured for complementary receipt of a distal threaded portion of an extension rod.

19. The system of claim 18, wherein the plurality of extension rods are selectively removable from the plurality of pedicle screws.

20. The system of claim 19, wherein each coupling member defines an aperture configured to receive the extension rod therethrough, and wherein the coupling member can be slidably moved along the extension rod for operative positioning about the proximal end of the pedicle screw.

21. The system of claim 20, wherein each coupling member comprises a distal body portion and a proximal body portion, wherein the distal and proximal body portions are hingeably connected to operatively define the socket portion of the coupling member.

22. The system of claim 21, wherein the distal and proximal body portions of each coupling member define an aperture configured for receiving the extension rod therethrough, and wherein each coupling member can be slidably moved along a respective extension rod for operative positioning about the proximal end of the pedicle screw to which the extension rod is operatively coupled.

23. The system of claim 22, further comprising a plurality of fasteners, each defining an aperture therethrough, wherein each fastener can be slidably moved along a respective extension rod for operative positioning about the proximal end of the pedicle screw to which the extension rod is operatively coupled.

24. The system of claim 23, wherein the proximal ends of the pedicle screws each comprise threaded portions configured for complementary engagement with the aperture of the fasteners.

25. The system of claim 24, wherein the plurality of fasteners can be tightened against the respective proximal body portions of the coupling members to adjust the respective rod clamps into their second clamped configuration.

26. The system of claim 24, wherein the plurality of fasteners can be loosened to adjust the respective rod clamps into their first configuration allowing slidable movement of the rod clamps along the support rod.

27. A method of implanting a spine stabilization system, comprising:
driving a plurality of pedicle screws therein predetermined locations along a subject's spinal column;
releasably mounting a distal end of an extension rod to a proximal portion of each of the pedicle screws, wherein a proximal end of each extension rod extends posterior to the skin of the subject;
mounting a plurality of rod clamps to a rigid elongated support rod;
providing a plurality of coupling members, each coupling member configured to engage a proximal portion of a pedicle screw;
mounting a socket engaging portion of each rod clamp therein a respective socket portion of each coupling member;
slideably mounting the plurality of coupling members onto the proximal ends of the plurality of extension rods;

sliding the plurality of coupling members down the respective extension rods into contact with the proximal portions of the pedicle screws;

providing a plurality of fasteners;

slideably mounting the plurality of fasteners onto the proximal ends of the plurality of extension rods and down the respective extension rods into contact with the proximal portions of the pedicle screws;

tightening the plurality of fasteners about the proximal portion of the pedicle screws and against portions of the respective coupling members to fix the respective rod clamps at predetermined positions along the support rod; and removing the plurality of extension rods from the plurality of pedicle screws.

* * * * *